US008538771B2

(12) United States Patent
Nagaeda

(10) Patent No.: US 8,538,771 B2
(45) Date of Patent: Sep. 17, 2013

(54) MEDICAL TREATMENT SUPPORTING METHOD AND MEDICAL TREATMENT SUPPORTING APPARATUS FOR MANAGING NURSING CARE ACTIONS

(75) Inventor: Tsuyoshi Nagaeda, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 990 days.

(21) Appl. No.: 11/820,466

(22) Filed: Jun. 19, 2007

(65) Prior Publication Data

US 2008/0021733 A1 Jan. 24, 2008

(30) Foreign Application Priority Data

Jul. 20, 2006 (JP) ................................. 2006-197685

(51) Int. Cl.
G06Q 10/00 (2012.01)
G06Q 50/00 (2012.01)
(52) U.S. Cl.
USPC ................................................. 705/2; 705/3
(58) Field of Classification Search
USPC ......................................................... 705/2, 3
See application file for complete search history.

(56) References Cited

U.S. PATENT DOCUMENTS

| 6,770,029 | B2 * | 8/2004 | Iliff | 600/300 |
|---|---|---|---|---|
| 7,299,192 | B2 * | 11/2007 | Luttrell | 705/3 |
| 7,577,573 | B2 * | 8/2009 | Janas et al. | 705/2 |
| 2007/0168231 | A1 * | 7/2007 | Sasai | 705/2 |
| 2008/0021738 | A1 * | 1/2008 | Komiya et al. | 705/3 |

FOREIGN PATENT DOCUMENTS

| JP | 11-282933 A | 10/1999 |
|---|---|---|
| JP | 11-282936 A | 10/1999 |
| JP | 2003-108661 | 4/2003 |
| JP | 2006-133910 A | 5/2006 |

OTHER PUBLICATIONS

Fujitsu Hope/NsMain for Windows-Nursing Plan Instruction Manual (Nursing Supporting System), Fujitsu Hope/NsMain for Windows-Nursing Plan Instruction Manual (Nursing Supporting System), Fujitsu Limited, Jun. 30, 1996, first edition, pp. 1-26, together with a partial English language translation.
Hope/Egmain-Ex Nursing Library Instruction Manual, Hope/Egmain-Ex Nursing Library Instruction Manual, Fujitsu Limited, Jun. 30, 2000, first edition, pp. 22-23, together with a partial English language translation.
Official Action, dated Apr. 19, 2011, from the Japan Patent Office in counterpart Japanese Patent Application No. 2006-197685, together with a partial English language translation.
Fujitsu Hope/NsMain for Windows-Nursing Plan Instruction Manual (Nursing Supporting System), Fujitsu Hope/NsMain for Windows-Nursing Plan Instruction Manual (Nursing Supporting System), Fujitsu Limited, Jun. 30, 1996, first edition, pp. 1-26, Jul. 19, 2011.
Hope/Egmain-Ex Nursing Library Instruction Manual, Hope/Egmain-Ex Nursing Library Instruction Manual, Fujitsu Limited, Jun. 30, 2000, first edition, pp. 22-23, Jul. 19, 2011.
Japanese Office Action, dated Dec. 20, 2011, issued in counterpart Japanese Patent Application No. 2006-197685.

* cited by examiner

*Primary Examiner* — Neha Patel
(74) *Attorney, Agent, or Firm* — Scully, Scott, Murphy & Presser, P.C.

(57) ABSTRACT

An operating apparatus receives implementation contents of a medical treatment performed on a patient. A recording unit records the received implementation contents. A management unit extracts evaluation data on an evaluation from the implementation contents recorded by the recording unit. The management unit adds the extracted evaluation data to an edit area and edits a summary of an implementation result of the medical treatment. The recording unit records a result of the editing carried out in the management unit.

3 Claims, 40 Drawing Sheets

PATIENT ID : 1234567
PATIENT NAME: TARO TOKYO

| ~100 | ~102 | ~104 | ~106 | ~108 | ~110 |
|---|---|---|---|---|---|
| ID NO. | NURSING PROBLEM | NURSING CARE PLAN | IMPLEMENTATION RESULT | NURSING RECORD | VARIANCE FACTOR |
| #1 | THERE IS A RISK OF SUFFERING FROM A HEMORRHAGIC SHOCK DUE TO HEMATEMESIS OR MELENA | (OP) ① VITAL SIGN | BODY TEMPERATURE: 36.5°C | [S] ... [O] ... [A] ... [P] | |
| #2 | THERE IS A POSSIBILITY THAT WATER BALANCE IS DISRUPTED BY THE LACK OF BLOOD | (OP) : | AMOUNT OF HEMATEMESIS: 50cc ... | [S] ... [O] ... [A] ... [P] | PATIENT/FAMILY (+) |
| : | : | : | : | : | : |
| #N | | | | | |

| PATIENT ID | PATIENT NAMES | SEX | AGE | ADMISSION DATE | EXPECTED DISCHARGE DATE | HOSPITAL DAYS | COMMENTS |
|---|---|---|---|---|---|---|---|
| 100001 | TARO KYOTO | M | 19 YEARS AND 6 MONTHS OLD | 2003/12/01 | 2003/12/21 | 12 DAYS | |
| 100002 | SABURO SHIGA | M | 22 YEARS AND 4 MONTHS OLD | 2003/12/02 | 2003/12/30 | 11 DAYS | |
| ⋮ | ⋮ | ⋮ | ⋮ | ⋮ | ⋮ | ⋮ | ⋮ |

| PATIENT'S ROOM | PATIENT ID | PATIENT NAMES | SEX | AGE | ADMISSION DATE | EXPECTED DISCHARGE DATE | HOSPITAL DAYS | COMMENTS |
|---|---|---|---|---|---|---|---|---|
| 420 | 1000001 | TARO KYOTO | M | 19YRS 6MTH | 2003/12/01 | 2003/12/21 | 12DAYS | |
| 420 | 1000002 | SABURO SHIGA | M | 22YRS 4MTH | 2003/12/02 | 2003/12/30 | 11DAYS | |
| 421 | 1000003 | HANAKO NARA | F | 67YRS 10MTH | 2003/12/11 | 2003/12/25 | 1DAY | |
| 421 | 1000004 | KIKUKO MIE | F | 42YRS 2MTH | 2003/11/23 | 2004/01/05 | 19DAYS | |
| 422 | 1000005 | MOMO ISHIKAWA | F | 44YRS 3MTH | 2003/11/01 | 2003/12/28 | 43DAYS | |
| 422 | 1000006 | MOMOKO TAKAMATSU | F | 56YRS 1MTH | 2003/12/09 | 2003/12/26 | 3DAYS | |
| 422 | 1000007 | SAKURA KANAZAWA | F | 67YRS 4MTH | 2003/12/07 | 2003/12/16 | 5DAYS | |
| 423 | 1000008 | HANAMI KANAGAWA | F | 67YRS 6MTH | 2003/12/06 | 2003/12/17 | 6DAYS | |
| 423 | 1000009 | JIRO NIIGATA | M | 87YRS 6MTH | 2003/11/21 | 2003/12/22 | 22DAYS | |
| 423 | 1000010 | SHIRO KUMAMOTO | M | 92YRS 8MTH | 2003/10/22 | 2003/12/20 | 54DAYS | |
| 423 | 2111111 | GORO IBARAKI | M | 32YRS 7MTH | 2003/12/01 | 2003/12/21 | 12DAYS | |
| 423 | 2111112 | TAICHI KAGAWA | M | 69YRS 6MTH | 2003/12/03 | 2003/12/25 | 9DAYS | |
| 423 | 2111113 | SHINJI | | YRS 9MTH | 2003/12/04 | 2003/12/18 | 8DAYS | |
| 424 | 2111114 | FUJIKO | | YRS 11MTH | 2003/11/29 | 2003/12/22 | 15DAYS | AWAY FROM HOSPITAL SINCE 11TH |
| 424 | 2111115 | KIKU G | | YRS 6MTH | 2003/11/25 | 2003/12/23 | 19DAYS | |
| 424 | 2111116 | YUMEKO | | YRS 2MTH | 2003/12/03 | 2003/12/27 | 10DAYS | |
| 424 | 2111117 | NOGIKU | | YRS 2MTH | 2003/12/06 | 2003/12/21 | 7DAYS | |
| 425 | 2111118 | KURUMI | | YRS 7MTH | 2003/12/10 | 2003/12/20 | 2DAYS | |

Popup menu:
- PLANNING
- ORDER ISSUE
- RECORD/EVALUATION
- TEMPRATURE PLATE
- PATIENT INFO
- DETAIL
- WRISTBAND PRINTING
- CANCEL

PATIENT SELECTION / PLANNING / ORDER ISSUE / RECORD/EVALUATION

WARD SOUTH-4 WARD

LOGOUT

| 130 | 132 | 134 | 136 |
|---|---|---|---|
| DEPARTMENT | DISEASE | NURSING PROBLEM | NURSING PROBLEM CODE |
| GASTROEN-TEROLOGY | ESOPHA-GITIS | ... | 0001 ... |
| | COLON CANCER | THERE IS A RISK OF SUFFERING FROM A HEMORRHAGIC SHOCK DUE TO HEMATEMESIS OR MELENA | 1000 ... |
| | | THERE IS A POSSIBILITY THAT WATER BALANCE IS DISRUPTED BY BLOOD LOSS | 1XXX |
| PEDIATRICS | ... | ... | 9000 ... |
| | | | 9XXX |

| NURSING PROBLEM CODE (140) | TARGET (142) | PLAN (144) |
|---|---|---|
| 1000 | FIND THE BLEEDING IN EARLY STAGES AND PREVENT A CRITICAL SHOCK STATE<br>◆FROM WHEN BLEEDING STARTS FROM ESOPHAGEAL VARIX UNTIL ARREST OF BLEEDING IS VERIFIED | (OP)<br>① VAITAL SIGN<br>　1) BP<br>　2) PULSE<br>　…<br>(CP)<br>① SECURE BLOOD VESSEL, EMERGENCY CART, PREPARATION OF A MONITOR<br>　…<br>(EP)<br>① NECESSITY OF BED REST DEPENDING ON MENTAL STATUS |
| 9XXX | . . . | . . . |

ENTER TEMPERATURE 36.5

| 7 | 8 | 9 | BS |
| 4 | 5 | 6 | |
| 1 | 2 | 3 | C |
| 0 | 00 | . | |

| CANCEL | SET |

TRANSMIT?

| HH:MM | ITEM NAME | MESURAD VALUES |
|---|---|---|
| 10:00 | BODY TEMPERATURE | 36.5°C |
| 10:01 | URINE VOLUME | 200cc |
| 10:02 | PULSE | 63 |

| CANCEL | SEND |

22

56

| VARIANCE | FACTORS | # OF TIMES |
|---|---|---|
| + | PATIENT/FAMILY | 13 |
| | MEDICAL STAFF MEMBER | 50 |
| | SYSTEM | 11 |
| | OTHER | 4 |
| − | PATIENT/FAMILY | 6 |
| | MEDICAL STAFF MEMBER | 10 |
| | SYSTEM | 48 |
| | OTHER | 2 |

170 — VARIANCE
172 — FACTORS
174 — # OF TIMES

(Rotated screen content)

SOUTH-4 WARD PATIENT ID 1234567 PATIENT NAME TARO TOKYO
ROOM 423 SEX MALE BIRTH DATE 1955/12/15 AGE 49YRS 6MTH BLOOD TYPE A (RH+) DETAIL

PATIENT SELECTION — PLANNING — ORDER ISSUE — RECORD/EVALUATION

PROBLEM LIST

| PROBLEM# | PROBLEM | PLANNING | | |
|---|---|---|---|---|
| #1 | THERE IS A RISK OF SUFFERING FROM A HEMORRHAGIC SHOCK DUE TO HEMATEMESIS OR MELENA | HANAKO TANAKA | | |
| #2 | THERE IS A POSSIBILITY THAT WATER BALANCE IS DISRUPTED BY BLOOD LOSS | HANAKO TANAKA | | |

PROBLEM# TARGET/EVALUATION

1 TARGET
FIND THE BLEEDING IN EARLY STAGES AND PREVENT A CRITICAL SHOCK STATE
◆ FROM WHEN BLEEDING STARTS FROM ESOPHAGEAL VARIX UNTIL ARREST OF BLEEDING IS VERIFIED
(EP)
⊙ MAINTAIN A SHOCK POSITION
(EP2)
⊙ NECESSITY OF BED REST DEPENDING ON MENTAL STATUS
(OP)
⊙ AT TIME OF HEMATEMESIS: NORMAL, OBSERVE ITS VOLUME

2 TARGET
TAKE A POSTURE TO PREVENT THE RISK OF ASPIRATION

NURSING RECORD — RECORDED BY

| DATE AND TIME | PROBLEM# ITEMS | S.O | A.P | |
|---|---|---|---|---|
| 10:02 | BODY TEMPERATURE #1 | 38.5°C [S] | [A] | HANAKO TANAKA |
| | | | [P] | |

☐ NURSING RECORD #1 [A:EVALUATION]
SUBJECTIVE INFORMATION ON A PATIENT IS DESCRIBED

— 300
— 302
— 304

EVALUATION | VARIANCE FACTOR
○ RESOLVED | ⊙ PATIENT/FAMILY
⊙ CONTINUE | ○ MEDICAL STAFF MEMBER
○ CHANGE | ○ SYSTEM
         | ○ OTHER

[CANCEL] [OK]

STORE TEMPORARILY | REGISTER

LOGOUT

FIG.44

MEDICAL TREATMENT SUPPORTING METHOD AND MEDICAL TREATMENT SUPPORTING APPARATUS FOR MANAGING NURSING CARE ACTIONS

CROSS-REFERENCE TO RELATED APPLICATIONS

This application is based upon and claims the benefit of priority from the prior Japanese Patent Application No. 2006-197685, filed Jul. 20, 2006, the entire contents of which are incorporated herein by reference.

BACKGROUND OF THE INVENTION

1. Field of the Invention

The present invention relates to a medical treatment supporting technique and it particularly relates to a medical treatment supporting method and a medical treatment supporting apparatus for managing nursing actions.

2. Description of the Related Art

Nursing care activities are conducted on patients having various kinds of diseases in hospitals. In general, the nursing care activities are conducted based on a nursing care plan for each of various nursing actions per patient and disease. In order to perform accurate nursing actions under these circumstances it is desirable that implementation results of nursing care plans be recorded and stored. For this reason, a personal computer (hereinafter referred to as "PC") displays the nursing care plans and receives the implementation results of nursing care plans carried out based on the displayed nursing care plans. Further, the PC records the received results (See Reference (1) in the following Related Art List, for instance).

RELATED ART LIST (1) Japanese Patent Application Laid-Open No. 2003-108661.

In a nurses' workflow starts with the gathering of information on patients and the extraction of nursing problems that the patients have. When the nurses prepare nursing care plans for the nursing problems and perform nursing actions based on the nursing care plans, they record the results thereof. Further, the nurses prepare nursing summaries at the time when patients are discharged from a hospital. Here, the nursing summary is a summary of contents recorded at the time of hospital admittance. This nursing summary will be used to grasp the contents of the current or past hospitalization when a patient will be readmitted or will be used to grasp quickly the conditions of a patient at a hospital where the patient is transferred. Like a nursing record, such a nursing summary is required to have complete details during hospitalization described therein. However, in the actual setting, each nurse often enters information into the nursing summary the way he/she himself/herself feels most appropriate. Accordingly, the quality of the nursing summaries changes from one nurse to another.

SUMMARY OF THE INVENTION

The present invention has been made in view of the foregoing circumstances, and a general purpose thereof is to provide a medical treatment supporting technology by which to prepare a nursing summary of a certain high quality where all required information is described.

In order to resolve the above problems, a medical treatment supporting apparatus according to one embodiment of the present invention comprises: an input unit which receives implementation contents of a medical treatment performed on a patient; a first recording unit which records the implementation contents received by the input unit; an extraction unit which extracts evaluation data on an evaluation from the implementation contents recorded by the first recording unit; an editing unit which adds the evaluation data extracted by the extraction unit to an edit area and which edits a summary of an implementation result of the medical treatment; and a second recording unit which records an editing result obtained by the editing unit.

According to this embodiment, when the summary of an implementation result is prepared, the evaluation data are added to the edit area. Hence, the evaluation data can be automatically added to the summary of an implementation result and therefore it is possible to prepare the summary of an implementation result having a certain high quality.

The first recording unit may further record a problem for the patient to whom the medical treatment is to be performed. Then the extraction unit may extract remaining unresolved problem data from among problems for the patient recorded in the first recording unit, and the editing unit may add the remaining unsolved problem data extracted by the extraction unit to the edit area. In this case, the remaining problem data are also added, so that problems for the patient which are to be resolved in the future can be clearly specified.

The apparatus may further comprise a verification unit which verifies a status in the medical treatment performed on a patient. When a verification result in the verification unit belongs to a case of a hospital discharge, the editing unit may add the evaluation data to the edit area; and when the verification result in the verification unit belongs to a case other than the hospital discharge, the editing unit may further add the remaining problem data to the edit area in addition to the evaluation data. In this case, the type of data added to the edit area is changed according to the status, so that a summary of the implementation result best suited for the status can be prepared.

The apparatus may further comprise a display unit which displays the remaining problem data added to the edit data by the editing unit in a manner that the remaining problem data added thereto are more emphasized than other display contents. In such a case, the remaining problem data are displayed in a manner that they are more emphasized than the other display contents, so that the attention can be drawn to the remaining problem data.

The apparatus may further comprise a management unit which manages items necessary for preparing the summary of an implementation result of the medical treatment. The editing unit compares data already added to the edit area with the necessary items managed by the management unit, and prompts addition of an item which has not yet been added. In such a case, the addition of items which have not yet been added is prompted, so that the items which should be added but have not yet been added can be prevented from not being added to the summary.

Another embodiment of the present invention relates to a method for supporting a medical treatment. This method comprises: receiving implementation contents of a medical treatment performed on a patient; recording the received implementation contents; extracting evaluation data on an evaluation from the recorded implementation contents; and adding the extracted evaluation data to an edit area and editing a summary of an implementation result of the medical treatment.

It is to be noted that any arbitrary combination of the above-described structural components or rearrangement in the form among a method, an apparatus, a system, a recording medium, a computer program and so forth are all effective as and encompassed by the present embodiments.

BRIEF DESCRIPTION OF THE DRAWINGS

Embodiments will now be described by way of examples only, with reference to the accompanying drawings which are meant to be exemplary, not limiting.

FIG. 3 illustrates a data structure of nursing information recorded in a recording unit of FIG. 2;

FIG. 5 illustrates a data structure of patient information recorded in a recording unit of FIG. 2;

FIG. 7 illustrates a screen, at a stage of patient selection, displayed on a display apparatus of FIG. 2;

FIG. 8 illustrates a data structure of a nursing problem database contained in a first database of FIG. 2;

FIG. 9 illustrates a data structure of a nursing care plan database included in a second database of FIG. 2;

FIG. 11 illustrates an initial screen, at a planning stage displayed, on a display apparatus of FIG. 2;

FIG. 12 illustrates a screen for a nursing problem selection displayed on a display apparatus of FIG. 2;

FIG. 13 illustrates a screen displayed after a nursing care plan displayed on a display apparatus of FIG. 2 has been entered;

FIG. 14 illustrates an additional window for a comment on a nursing problem displayed on a display apparatus of FIG. 2;

FIG. 15 illustrates a screen displayed after a comment on a nursing problem displayed on a display apparatus of FIG. 2 has been entered;

FIG. 17 illustrates a screen after a nursing care plan displayed on a display apparatus of FIG. 2 has been edited;

FIG. 22 illustrates a screen displayed on a display apparatus of FIG. 2 at a stage of order issuing;

FIG. 25 illustrates an entry screen of an implementation result displayed by a PDA of FIG. 1;

FIG. 26 illustrates a send screen for an implementation result displayed by a PDA of FIG. 1;

FIG. 33 illustrates an initial screen obtained when an evaluation is entered and displayed on a display apparatus of FIG. 2;

FIG. 34 illustrates an input screen of subjective information displayed on a display apparatus of FIG. 2;

FIG. 35 illustrates an entry screen of evaluation information displayed on a display apparatus of FIG. 2;

FIG. 38 illustrates a screen obtained after a nursing care plan displayed on a display apparatus of FIG. 2 has been entered;

FIG. 43 illustrates an initial screen of a nursing summary displayed on a display apparatus of FIG. 2; and FIG. 44 illustrates a screen of a nursing summary displayed on a display apparatus of FIG. 2.

DETAILED DESCRIPTION OF THE INVENTION

Figure 1:
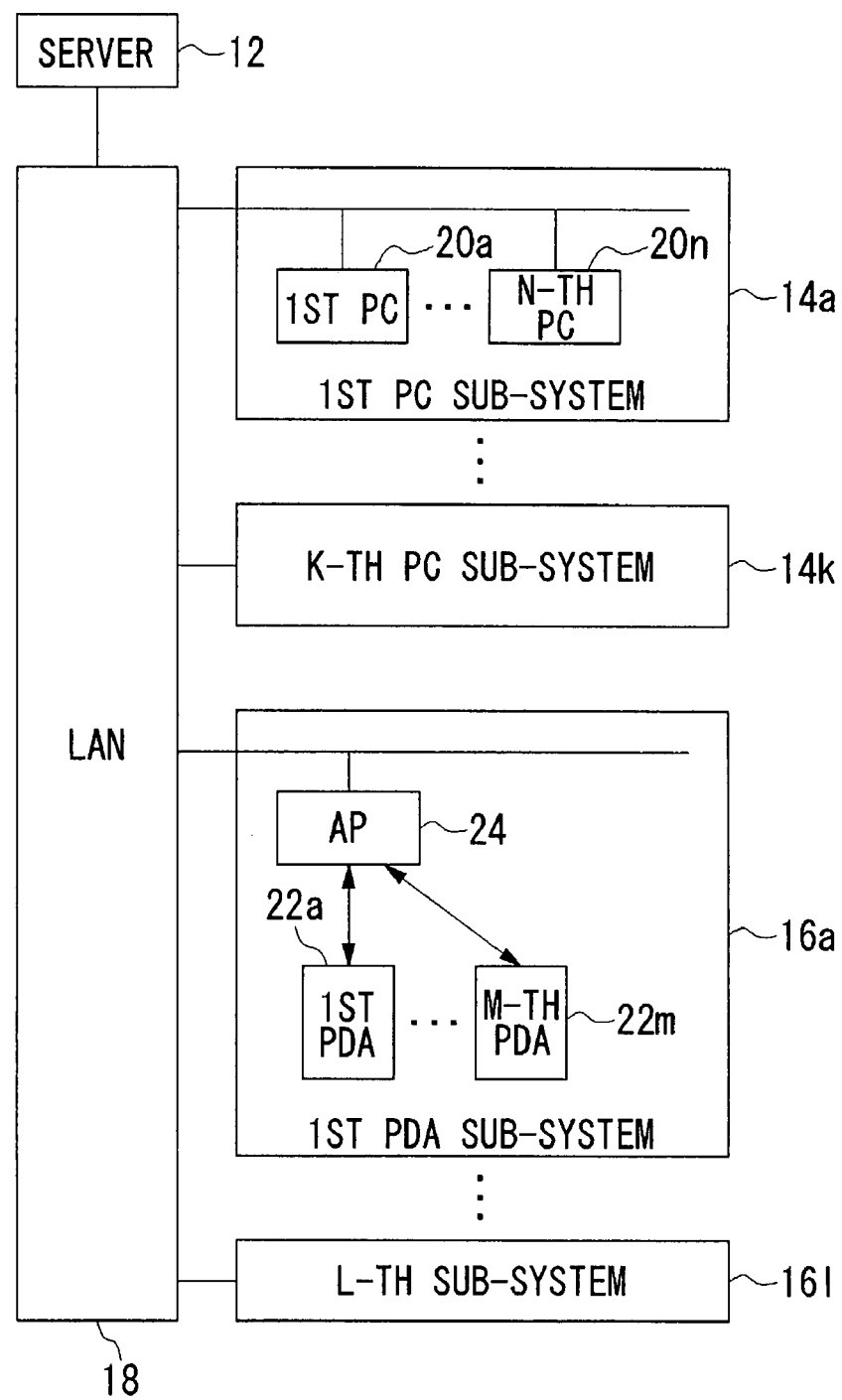
FIG. 1 illustrates a nursing information management system according to an exemplary embodiment of the present invention.

The invention will now be described by reference to the preferred embodiments. This does not intend to limit the scope of the present invention, but to exemplify the invention.

An outline of the present invention will be given before a specific description thereof. Exemplary embodiments of the present invention relate to a nursing system for managing nursing actions performed on patients and nursing actions yet to be performed on the patients. A nursing information management system includes PCs installed in a nurses' station and the like, PDAs carried by nurses and a server for recording data used in the nursing information management system, and all of these are connected with one another via a LAN. The nursing information management system is characterized mainly by the following features.

The first feature is that a plurality of stages are defined for a nursing care activity and the nursing care activity is managed by relating each of stages to one another. Since the plurality of stages are so structured as to be cyclic, ongoing nursing care activity implementation contents can be determined with the past nursing care activity implementation contents taken into consideration. The second feature is that the screen of a PC is structured so that nursing care activity contents at the plurality of stages can be read through. The nurses use PDAs while performing nursing care activities, but they basically use PCs when doing activities other than the nursing care activities. By employing the structure of a screen as above, the nursing care activity contents can be verified and determined by relating each of the plurality of stages to one another.

Third feature is that since adjacent two stages among the plurality of stages must have a relevancy to each other, once one of them having the relevancy is determined, the contents thereof is automatically reflected in the other. As a result, the entry of the other is supported and therefore the load of the entries and possible entry mistakes can be reduced. The fourth feature is that in a case when there is discrepancy between a patient's recovery schedule and an actual recovery, a factor attributed thereto is also entered. By analyzing the discrepancy, the contents of nursing care activities can be improved. The fifth features is to prepare an initial "edit content" of a nursing summary that summarizes a recording content at the time of hospital admittance based on implementation results of nursing care items recorded already. Further, a nurse prepares a final nursing summary by editing the initial edit contents. Automatic preparation of the initial edit contents of a nursing summary allows maintaining a certain high quality for the nursing summary.

With the above-described features, a general purpose of the nursing information management system according to the embodiments is to provide proper nursing care actions. The following background lies behind this purpose. Under the current health-care system after a reform, strict management of revenue and expenditure is required in hospitals. Given the importance of managing a hospital, the hospital tends to suppress the expenditure. In the current health-care system, the prolonged duration of patient hospitalization will increase the hospital's expenditure. For this reason, it is desired that the nursing care actions be so improved that the length of hospital stay for a patient be shortened. This is beneficial not only from the standpoint of hospitals but also from the standpoint of patients.

A nursing information management system will now be described below. To clarify a description, the entire description is divided into six sections. In section (1), a general outline of the nursing information management system is described, and each part included in the nursing information management system will be described in sections (2) to (7).

1. General structure

A description of terminologies defined in the nursing information system will be given before a description of a structure of the nursing information management system. "Nursing problem" indicates a symptom to be taken care of by a nursing care, and this corresponds to a problem to be resolved by a nurse's proactive action. Examples of the nursing problems include "there is a concern about rebleeding and its treatment", "comfortable environment cannot be maintained due to hematemesis and melena" and "mental turmoil is inevitable as a result of massive hematemesis and melena", which are problems all adversely effecting the degree of recovery of a patient. If the nursing problem involves a plurality of items, each will be indicated as "nursing problem item".

"Nursing care plan" indicates a nursing policy for a patient and it corresponds to a plan for a nursing care. The nursing care plan includes four items, namely, (1) a plan to resolve a problem deterring a planned target, (2) an effect expected when it is resolved, (3) a targeted patient condition and (4) an evaluation. A planned target indicates a condition expected for a nursing problem, and corresponds to a desirable patient condition. Examples of targets include "can accept and live with the disease", "can understand the necessity of a long period of treatment and participate positively in the treatment" and "be aware of and have motivation toward self-care and can take daily-life action suited for a symptom".

The plan include an observation plan (OP), a care plan (CP), and an education-guidance plan (EP). OP indicates an observation item for determining a course, CP indicates a medical care, a therapy, a treatment and the like, EP indicates education regarding knowledge, method, technique and the like necessary for coping with the problem prevention, alleviation and resolution for oneself. Examples of OP include "blockage of upper respiratory tract and respiratory discomfort during the night (tongue being flatly positioned toward the back of the mouth; irregular respiration with stertor)" and "respiratory condition (respiration frequency, depth, rhythm, chest motion, the presence or absence of dyspnea on effort". Examples of CP include "a body posture is maintained where there is no strain to the chest motion" and "coughing is encouraged and, at the time of coughing, assist a patient to hold the abdomen tight by both hands". One example of EP is "explain the condition of disease to a patient and his/her family members and ask for their cooperation".

"Nursing items" indicate contents of a nursing care for a patient. The nursing items are contained in the nursing care plan and correspond to the above-described plan. Here, the nursing item includes OP, CP and EP contained in the above-described plan. Note that the nursing item may contain contents other than the above-mentioned ones and it may be any contents as long as it is to be performed by a nurse.

The problems to be resolved here may be indicated as follows. In order for the nursing contents to be most appropriate, it is desired that the correspondence between the nursing contents and the results thereof be clarified. It is desired that mistakes be minimized. It is also desired that alteration of the nursing contents be prevented. It is desired that the responsibility of nurses be clarified as to correction works for the recorded nursing contents. It is also desired that the patient hospitalization length be minimized.

FIG. 1 illustrates a nursing information management system 100 according to an exemplary embodiment of the present invention. The nursing information management system 10 includes a server 12, a first PC subsystem 14a, . . . and a Kth PC sub-system 14k, which are generically referred to as "PC sub-system 14", a first PDA sub-system 16a, . . . and an Lth PDA sub-system 161, which are generically referred to as "PDA sub-system 16", and a LAN 18. The first PC sub-system 14a includes a first PC 20a, . . . and an Nth PC 20n, which are generically referred to as "PC 20". The first PDA sub-system 16a includes an AP (Access Point) 24, a first PDA 22a, . . . an Mth PDA 22m, which are generically referred to as "PDA 22". For clarify of the Figure, the description of the structure of the PC sub-system 14 and the PDA sub-system 16 except for the first PC sub-system 14a and the first PDA subsystem 16a is omitted. It is assumed, however, that the structures for those omitted in FIG. 1 are the same as those of the first PC sub-system 14a and the first PDA sub-system 16a.

The PC sub-system 14, which includes a plurality of PCs 20, is provided in a nurses' station, for instance. The respective PC sub-systems 14 are connected to one another via the LAN 18, and the PCs 20 in each PC sub-system 14 are also connected to one another. In the nurses' station, medical staff members, such as nurses, enter data, refer to and verify the data or perform other tasks. The PC 20 supports the nurses in preparing the nursing problem items, supports the preparation of nursing care plans based on the thus prepared items for nursing problems and then specifies the implementation of nursing items contained in the prepared nursing care plans.

Here, in a case when "nursing problem item" contains a plurality of items, the items correspond respectively to the nursing problem items. "Supporting in preparing the nursing problem items" and "support of the preparation of nursing care plans" correspond to the implementation of processings, such as supporting the preparation by the PC 20 when a nurse prepares for a nursing problem and a nursing care plan. Though the detail will be discussed later, the preparation of a nursing care plan is supported by conducting search through a database based on the nursing items prepared for a patient. Here, the database contains nursing care plan items which are respectively associated beforehand with a plurality of kinds of items to be included in the nursing problem.

The PDA sub-system 16 is provided in places, where a nursing care is performed, such as a patient's room, an examination room, an operation room and the like, and the PDA sub-system 16 includes an AP 24 and a PDA 22. The PDA 22 and the AP 24 are connected via a wireless LAN. The PDA sub-system 16 is connected with the PC sub-system 14 via the LAN 18. The PDA 22 has normal PDA functions which include a means, for inputting data, such as a touch panel, a processing means, such as a CPU, for processing the inputted data, a means for storing the data, and a display means for displaying the processed data and the like. The PDA 22 has a communication function using a wireless LAN and a means for reading identification information, such as an identification code reader capable of reading the identification information. The identification information reading means may be an OCR (Optical Character Reader) which optically reads characters, an image scanner which reads in the characters or graphics as an image, a transponder which can read in the identification information by a wireless communication or the like. The identification information may be entered by a user.

The PDA 22, which is equipped with a communication function of a wireless LAN, can access the LAN 18 within a coverage area provided by the AP 24. As a result, the PDA 22 accesses the PC 20 and the server 12 to acquire the nursing care plan items, and then displays the acquired nursing care plan items on a display unit of the PDA 22. The nurse verifies the nursing care plan items displayed on the display unit of the PDA 22 and performs a nursing care according to the nursing care plan items. The nurse also enters implementation results of the nursing items. The PDA 22 transmits the implementation results to the PC 20.

The PC 20 receives the implementation results from the PDA 22. Further, the evaluations for the implementation results of nursing items are entered into the PC 20 by the nurse. The "evaluation" includes subjective and objective evaluations for a patient. The detailed description thereof will be given later. The PC 20 stores the entered evaluations, and the implementation results entered via the PDA 22 are recorded in memory. The PC 20 selects an implementation result that meets a predetermined condition, from among the implementation results recorded in memory, and then displays it on a partial area of screen. The implementation result is displayed on a partial area of screen, and other information such as nursing problems and nursing care plans is displayed on the other areas of screen.

Furthermore, while inputting the evaluations, when there is a discrepancy between an implementation result of a nursing item and a planned target in the nursing item specifying an implementation, the PC 20 also inputs information on a contributing factor of the discrepancy (hereinafter referred to as "variance factor") and records this factor by associating it with the evaluation. Here, the variance factor includes a case where the implementation result shows a more desirable result than the planned target (hereinafter referred to as "positive variance") and a case where the implementation result shows a worse result than the planned target (hereinafter referred to as "negative variance"). The case where the implementation result shows a more desirable result than the planned target corresponds to a case where the actual hospital discharge date comes earlier than a predetermined scheduled hospital discharge date. That is, it means that the recovery is faster than expected.

The server 12 stores data used in the nursing information management system 10. Although it is assumed herein that a single server 12 is provided, a plurality of servers 12 may be provided in the nursing information management system 10. In such a case, the servers 12 may be included in the PC sub-system 14. Furthermore, a hierarchical structure may be formed by a plurality of servers 12. In the following description, a description will be given on the assumption that data are communicated between the PC 20 and the PDA 22, for clarity of explanation. However, these data may be communicated between the PC 20 and the PDA 22 via the server 12. Also, the contents of data recorded in the server 12 and the contents of data recorded in the PC 20 may be subjected to a processing by using a known technique so that they are the identical data.

The PC sub-system 14 and the PDA sub-system 16 correspond, more specifically, to an out-patient system where the registration or the like of orders for injection and so forth is made, a ward system, a pharmaceutical division system where medicines are dispensed and paid out based on the registration of orders like an injection, a medical system where an account processing or the like for medical actions is carried out, a nursing system (or nurses' station system) where nurses perform mixture injections, and the like. The present embodiment relates to a nursing system. In particular, each nurse carries the PDA with her/him in a nurses' station or a ward where nurses conduct nursing care actions, and he/she goes to a place where a nursing action is conducted, namely the bedside of a hospitalized patient. At this spot, data on the particular medical action are inputted and outputted. As a result thereof, the conditions and states of nursing care actions are recorded in a real-time manner and grasped.

Figure 2:
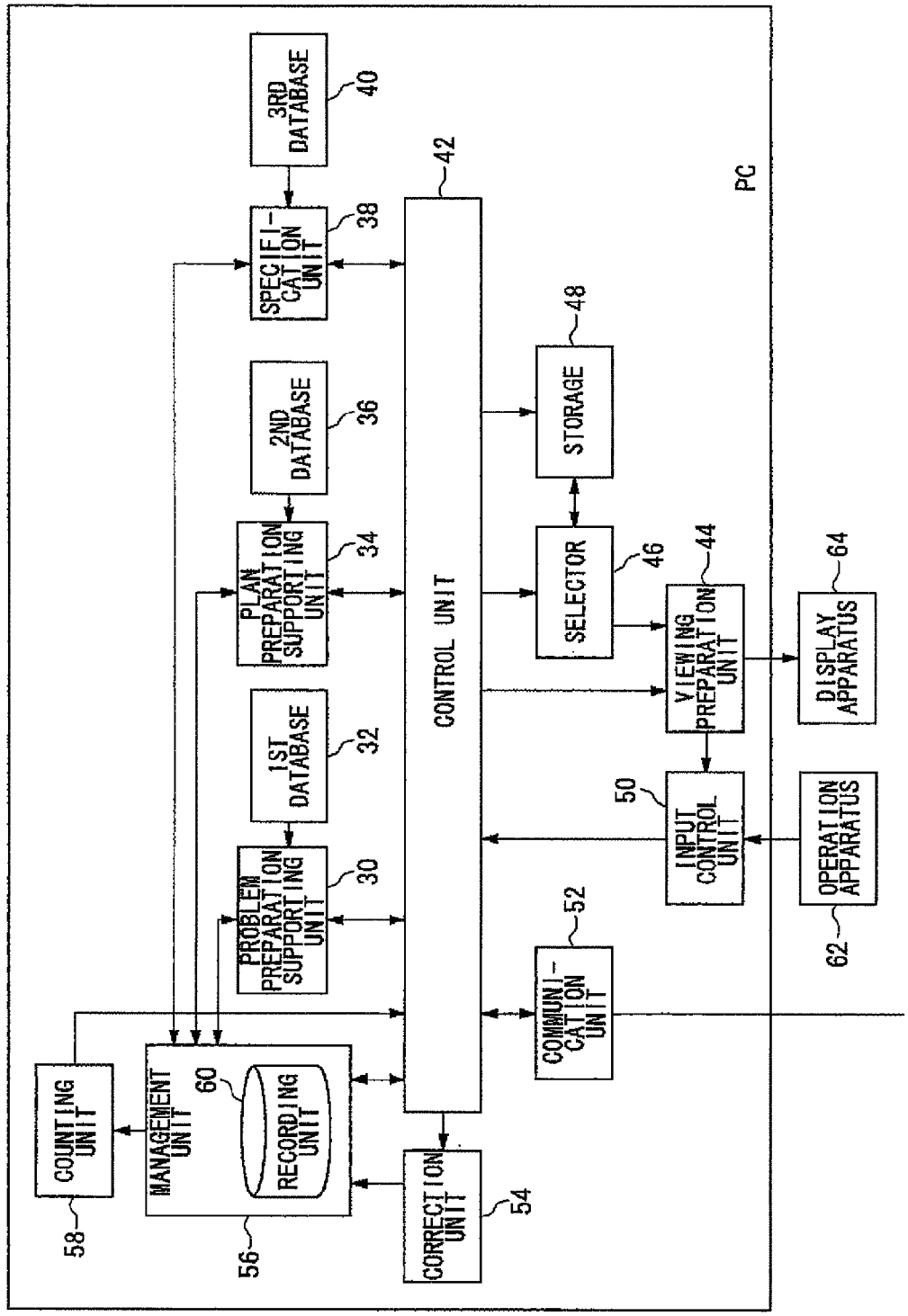
FIG. 2 illustrates a structure of a PC shown in FIG. 1.

FIG. 2 illustrates a structure of the PC 20. The PC 20 includes a problem preparation supporting unit 30, a first database 32, a plan preparation supporting unit 34, a specification unit 38, a third database 40, a control unit 42, a viewing preparation unit, a selector 46, a storage 48, an input control unit 50, a communication unit 52, a correction unit 54, a management unit 56, and a counting unit 58. The management unit 56 includes a recording unit 60. The PC 20 is connected with an operation apparatus 62 and a display apparatus 64.

The display apparatus 64 displays predetermined information. The display apparatus 64 may be structured integrally with the PC 20. The viewing preparation unit 44 generates a screen to be displayed on the display apparatus 64. The viewing preparation unit 44 receives information necessary for generating a screen to be displayed, from the control unit 42. In the present embodiment, a screen generated by the viewing preparation unit 44 is so structured as to be able to read through the respective contents at a plurality of nursing stages. The structure of this screen will be discussed later.

The operation apparatus 62 is operated by a nurse and inputs predetermined information to the PC 20. The operation apparatus 62 is comprised of a keyboard, a mouse and so forth. The operation apparatus 62 may also be integrally structured with the PC 20. The input control unit 50 outputs the received information to the control unit 42. In general, while verifying the screen displayed on the display apparatus 64, a nurse enters predetermined information using the operation apparatus 62. Accordingly, in order to recognize which part of the screen corresponds to the information inputted by the operation apparatus 62, the input control unit 50 receives information on a screen structure from the viewing preparation unit 44.

Figure 18:
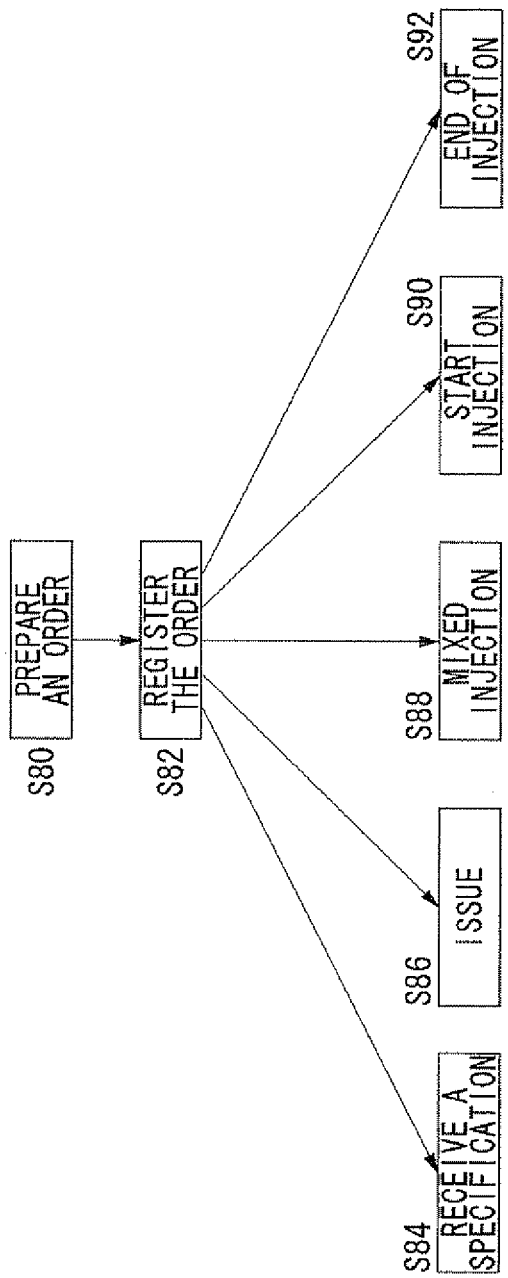
FIG. 18 is a schematic view showing an order issuance processing in a nursing information management system of FIG. 1.

The communication unit 52 is connected with the LAN 18 of FIG. 18, and communicates with the server 12, other PCs 20 and the PDA 22. The communication unit 52 receives information to be transmitted, from the control unit 42 and outputs the received information to the control unit 42. The communication unit 52 communicates with the PDA 22 at a predetermined timing to establish a data synchronism between the PC 20 and the server 12. The control unit 42 controls the input and output of predetermined information between components included in the PC 20. That is, the control unit 42 receives information from one component and then outputs the information to the another component. It is assumed that one component and another component are switched as appropriate. Accordingly, the control unit 42 has a switching function. For clarity of explanation, operations of one component and another component will be described hereinbelow, and the description of the control unit 42 is omitted.

The problem preparation supporting unit 30 supports the preparation of nursing problem items for a patient. In cooperation with the first database 32, the problem preparation supporting unit 30 outputs options necessary for preparing the nursing problems to the display apparatus 64. Subsequently, the problem preparation supporting unit 30 receives the selected options from the operation apparatus 62. By repeating the above operation, the problem preparation supporting unit 30 supports finally the preparation of nursing problem items. Also, the problem preparation supporting unit 30 receives comments to the thus prepared nursing problem items. The problem preparation supporting unit 30 outputs the thus prepared nursing problems items to the plan preparation supporting unit 34 and the recording unit 60, for example. A structure is such that these outputs from the problem preparation supporting unit 30 are fed thereto by way of the control unit 42 and the management unit 56.

The plan preparation supporting unit 34 supports the preparation of a nursing care plan based on the prepared nursing problem items. The plan preparation supporting unit 34 extracts a nursing care plan corresponding to the prepared nursing problem items, by searching through the second database 36 using the prepared nursing problem items. The contents of data contained in the second database 36 will be discussed later. The plan preparation supporting unit 34 displays the extracted nursing care plan on the display apparatus 64. Further, the plan preparation supporting unit 34 receives comments to the prepared nursing care plans. The plan preparation supporting unit 34 outputs the prepared nursing care plan to the recording unit 60.

In cooperation with the third database 40, the specification unit 38 specifies an implementation of nursing items contained in the nursing care plan. The specification unit 38 transmits the specification of an implementation of nursing items via the communication unit 52. The specification unit 38 may display a specification of nursing items on the display apparatus 64. When the specified nursing item is conducted by a nurse, the nurse enters the result into the PDA 22, and then PDA 22 transmits the implementation result of the nursing items to the communication unit 52. Upon receipt of the implementation result of the nursing items, the communication unit 52 outputs it to the recording unit 60. Further, the nursing result stored in the recording unit 60 is displayed on the display apparatus 64. In so doing, a nursing result to be displayed on the display apparatus 64 is selected by the selector 46 and the storage 48.

The nurse enters an evaluation of the implementation result of nursing items into the operation apparatus 62. The entered evaluation is recorded in the recording unit 60. Among the nursing problem items stored in the recording unit 60, the nursing items contained in the nursing care plan, the implementation results and the evaluations, the management unit 56 relates the mutually corresponding items with one anther, by a series of identifiers. That is, if, for example, "#1" serving as an identifier is assigned to an item of the nursing problems, then "#1" will also be assigned to the nursing items contained in a nursing care plan, the implementation results and the evaluations corresponding to this nursing problem item. As a result, a screen is created so that the nursing problem items, the nursing items contained in the nursing care plan, the implementation results and the evaluations are integrally contained within a single screen. Linked with the entered evaluations, another nursing care plan is inputted to the recording unit 60. The processings performed subsequent to the inputted nursing care plan are the same as those described so far and therefore the repeated description thereof is omitted here. Note that it suffices if the recording unit 60 has a function of storing predetermined information, and the recording unit 60 includes a hard disk or RAM (Random Access Memory). Moreover, the recording unit 60 may be structured by a plurality of recording media, for example, a hard disk and a RAM. For simplicity, no distinction will be made hereinafter therebetween.

The correction unit 54 receives corrections corresponding to at least one of the nursing problem item recorded in the recording unit 60, the nursing item contained in a nursing care plan, the implementation result and the evaluation. In so doing, alteration by the third parties is prevented. Hence, the correction unit 54 performs a management in such a manner that the history of corrections is not deletable. For example, the correction unit 54 manages the history of corrections and, in so doing, it manages also the dates of correction and the persons who enter the correction.

When an evaluation is entered, there are cases where a variance factor is entered into the operation apparatus 62. Though a description will be given later of the variance factor, the recording unit 60 records the variance factors by associating them with nursing problem items and nursing items, implementation results and evaluations contained in a nursing care plan. The counting unit 58 performs a predetermined counting processing on the variance factors recorded in the recording unit 60.

In terms of hardware, this structure described as above can be realized by a CPU, a memory and other LSIs of an arbitrary computer. In terms of software, it can be realized by memory-loaded programs which have a reserved management function or the like, but drawn and described herein are function blocks that are realized in cooperation with those. Hence, it is understood by those skilled in the art that these function blocks can be realized in a variety of forms such as by hardware only, software only or the combination thereof.

FIG. 3 illustrates a data structure of nursing information recorded in the recording unit 60. FIG. 3 illustrates the nursing information for a single patient but the recording unit 60 records the nursing information corresponding to a plurality of patients. The nursing information contains an identification number space 100, a nursing problem space 102, a nursing care plan space 104, an implementation result space 106, a nursing record space 108, and a variance factor space 110. The identification numbers assigned by the management unit 56 are recorded in the identification number space 100. A nursing problem item, a nursing item contained in a nursing care plan, an implementation result, an evaluation and a variance factor corresponding to a predetermined identification number are recorded in the nursing problem item space 102, the nursing care plan space 104, the implementation result space 106, the nursing record space 108 and the variance factor space 110, respectively. The contents of the nursing care plan space 104, the implementation result space 106, the nursing record space 108 and the variance factor space will be discussed later.

Figure 4:
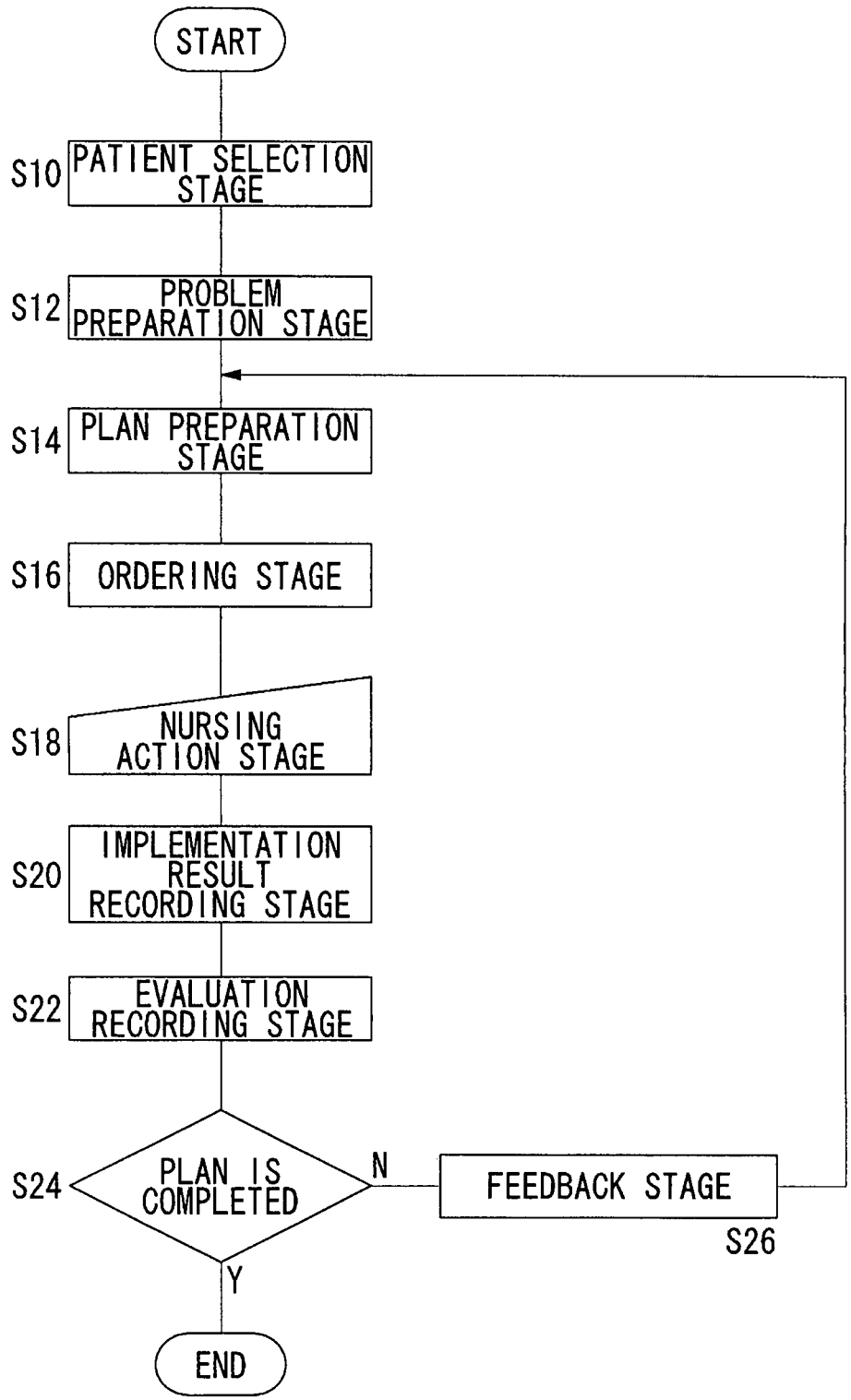
FIG. 4 is a flowchart showing a procedure for managing the nursing information in the nursing information management system of FIG. 1.

FIG. 4 is a flowchart showing a procedure for managing the nursing information in the nursing information management system 10. Each step in the flowchart corresponds to each of a plurality of stages defined for a nursing care. The management unit 56 executes a patient selection stage (S10). The patient selection stage corresponds to a stage where information on a single patient is selected from among information on a plurality of patients recorded in the recording unit 60. In so doing, the nurse selects a patient using the operation apparatus 62. The problem preparation supporting unit 30 executes a problem preparation stage (S12). The problem preparation stage corresponds to a stage where items for a nursing problem are prepared. The plan preparation supporting unit 34 executes a plan preparation stage (S14). The plan preparation stage corresponds to a stage where nursing care plans are prepared. The specification unit 38 executes an order stage (S16). The order stage corresponds to a stage where the implementation of nursing items are specified. At this stage, orders are issued and the contents of nursing items are outputted to the PDA 22.

The nurse performs a nursing care action stage (S18). The nursing care action stage corresponds principally to a stage where a human-induced task is conducted. The PDA 22 and the recording unit 60 execute an implementation result recording stage (S20). The implementation result recording stage corresponds to a stage where the nurse enters an implementation result into the PDA 22, the communication unit 52 receives this implementation result and then the recording unit 60 records the implementation result. The recording unit 60 executes an evaluation recording stage (S22). The evaluation recording stage corresponds to a stage where the recording unit 60 records variance factors via the operation apparatus 62. At this stage, the management unit 56 receives an input as to whether a nursing care plan is to be terminated or not. If the plan is to be terminated (Y of S24), the processing will be terminated. If the plan is not completed (N of S24), the management unit 56 and the like will execute a feedback stage (S26). The feedback stage corresponds to a stage where the processing from Step 14 onward is repeated. In so doing, the nursing care plan may be amended or revised and another nursing care plan may be newly added.

A description will now be given of an operation of the nursing information management system 10 structured as above. The nurse operates the PC 20 installed in the nurses' station and selects a patient or patients to whom a nursing care is to be provided. The nurse prepares nursing problem items using the PC 20, where a nursing care plan is prepared based on the thus prepared nursing problem items. The nurse issues an order to the server 12 from the PC 20, by referring to nursing items contained in the nursing care plan. The order is also sent to the PDA 22. While verifying the nursing items displayed on the PDA 22 in a patient's room, the nurse performs nursing care actions. Further, the nurse enters an implementation result of the nursing care actions into the PDA 22 from which the implementation result is sent to the PC 20. The nurse returns again to the nurse's station and enters an evaluation into the PC 20. The PC 20 records the implementation result received from the PDA 22 and the evaluation by associating them with each other. Also, a nursing care plan is added based on the evaluation.

By employing the above structure, a plurality of stages are defined for a nursing care and the management is performed by relating the plurality of stages to one another, so that the relationship between the nursing contents and the nursing results can be clarified. Also, since the relationship between the nursing contents and the nursing results is clarified, nursing contents required to yield a predetermined nursing result can be grasped. Also, more appropriate nursing contents can be derived by improving the contents. The improvement of the nursing contents can lead to shortening the length of patient hospitalization. The reduced duration of patient hospitalization is also desirable for the patient himself/herself. Since items related to one another, among the items for a nursing problem, the nursing items contained in a nursing care plan and evaluations, are brought into correspondence with one another by the use of a series of identifiers, the occurrence of mistakes in managing these items can be reduced. Also, the management of these items can be facilitated. Since the history of corrections is so managed as not to be deletable, the alteration of the nursing contents can be prevented. With this correction, if any inconvenience is caused in a nursing care, such a particular correction can be specified. Also, this draws the nurses' attention to the correction. Also, shared responsibility by nurses for the corrections can be clarified.

Since the difference between time when a nursing care action to be recorded takes places and time when an actual nursing care action takes place becomes smaller, so that the nursing care actions can be recorded and grasped with accuracy. Since the nurse verifies, by a PDA, the contents of work schedule for nursing care actions at a site where the nursing care actions are conducted, the accuracy of nursing care actions can be enhanced. Since the nurse enters the implementation result at once at the site the nursing care actions take place, the entry can be made with accuracy. Since the nurse verifies, by the PDA, the contents of nursing care actions in arbitrary places at any time, the nursing care action is conducted smoothly. Even in a case where the contents of nursing care actions are changed, the changed contents of nursing care actions can be appropriately dealt with if the nurse uses the PDA at the implementation site and verifies the changed contents of nursing care actions before conducting a nursing care. Since the nursing information management system accurately records the implementation result, an administrator and the like can improve the system by analyzing the recorded data later to achieve a further suitable state.

2. Patient Selection

Patient selection corresponds to Step 10 in FIG. 4. Problems to be resolved here may be expressed as follows. It is desired that the selection of patients be made in a simplified manner. Also, it is desired that the selection of patients be made accurately. To select patients, the viewing preparation unit 44, the display apparatus 64, the operation apparatus 62, the input control unit 50, the control unit 42, the management unit 56 and the recording unit 60 in FIG. 2 are principally used here.

The recording unit 60 records patient information. FIG. 5 illustrates a data structure of patient information recorded in the recording unit 60. The patient information includes a patient ID space 112, a patient name space 114, a gender space 116, an age space 118, an admission date space 120, an expected discharge date space 122, a hospital days space 124, and a comment space 126. The patient ID space 112 records identification numbers assigned to patients, and the patient name space 114 records names of patients. The gender space 116 records the gender of patients, and the age space 118 records the age of patients. The admission date space 120 records dates when patients are admitted to a hospital; the expected discharge date space 122 records dates of expected discharge of patients; and the hospital days space 124 records the number of days for which each patient has been hospitalized. The comment space 126 records comments to patients. The patient information recorded in the recording unit 60 may includes information other than these pieces of information mentioned above. For example, a basic patient profile, such as family structure, occupation and hospital ward, a patient record, a lifestyle habit of each patient before admittance, a background to hospital visiting, a daily action, or a mental side of each patient may be added as the patient information.

The viewing preparation unit 44 displays the listing of patient information recorded in the recording unit 60. The input control unit 50 receives from the operation apparatus 62 an instruction to select a single patient from the patient information. Based on the instruction received by the input control unit 50, the management unit 56 selects patient information and nursing information for a single patient, from the recording unit 60.

Figure 6:
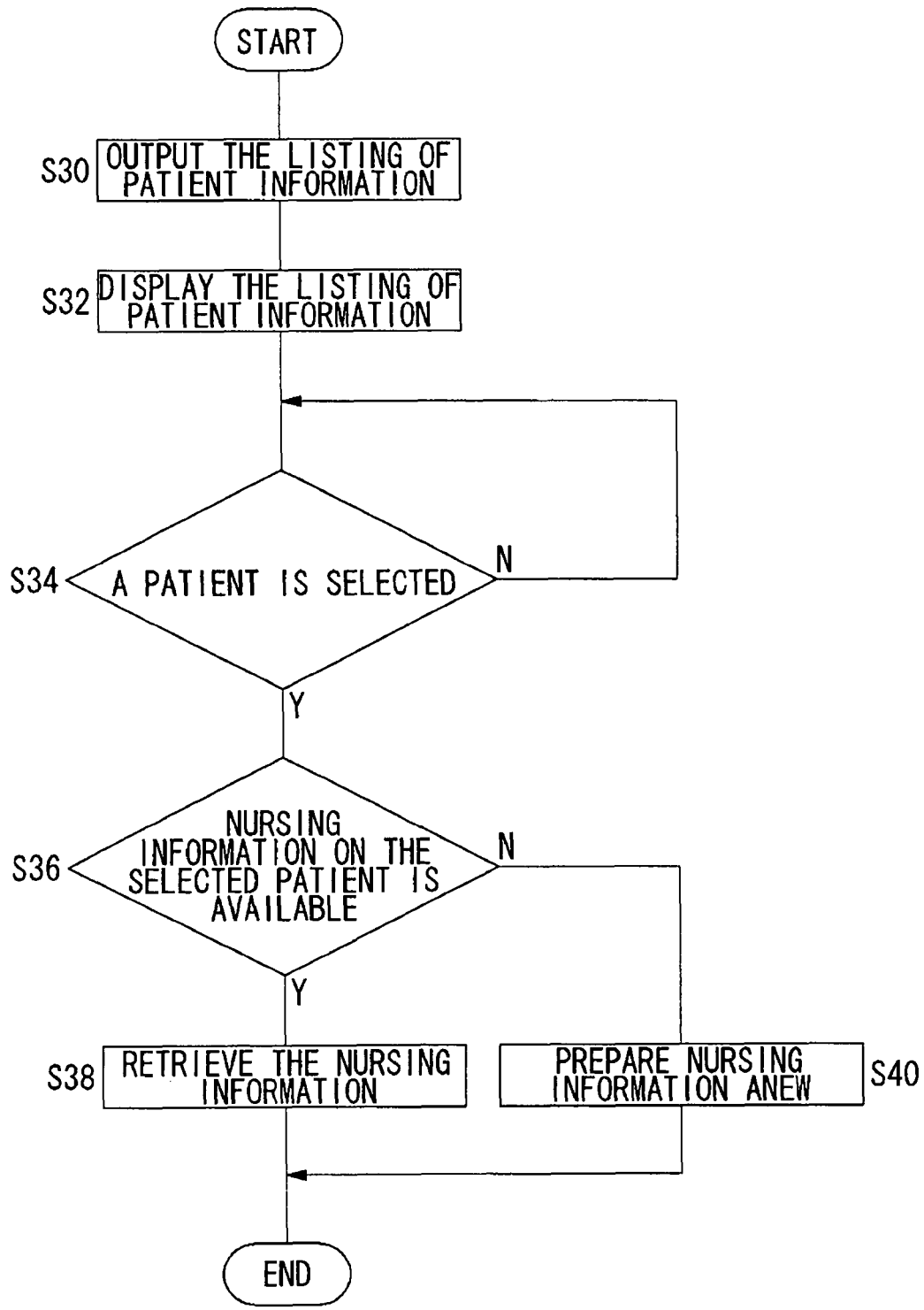
FIG. 6 is a flowchart showing a procedure for selecting patient information in a PC of FIG. 1.

FIG. 6 is a flowchart showing a procedure for selecting patient information in the PC 20. The management unit 56 outputs the listing of the patient information recorded in the recording unit 60 (S30). The viewing preparation unit 44 has the display apparatus 64 display the listing of the patient information (S32). FIG. 7 illustrates a screen, at a stage of patient selection, displayed on the display apparatus 64. Arranged on the screen are a patient selection button 200, a planning button 202, an order issuing button 204 and a recording/evaluation button 206. At a stage of patient selection, the patient selection button 200 is selected. The screen contains a patient's room space 208, a patient ID space 210, a patient name space 212, a gender space 214, an age space 216, an admission date space 218, an expected discharge date space 220, a hospital days space 222, and a comment space 224. Such contents correspond to the patient information recorded in the recording unit 60.

Refer back to FIG. 6, if the patient has not been selected by the operation apparatus 62 (N of S34), a wait state continues until selection is done. If, on the other hand, the patient is selected (Y of S34), the input control unit 50 receives selection information. In FIG. 7, the nurse selects a single patient "Taro Tokyo" using the operation apparatus 62. Refer back to FIG. 6. If nursing information for the selected patient is available in the recording unit 60 (Y of S36), the management unit 56 will retrieve the corresponding nursing information (S38). If the nursing information for the selected patient is not available in the recording unit 60 (N of S36), the management unit 56 prepares new nursing information (S40).

An operation of the PC 20 structured as above is now described. The nurse decides on a patient to whom a nursing care is to be conducted, from the listing of patient information displayed on the display apparatus 64. The nurse operates the operation apparatus 62 and selects the patient thus decided. Then, nursing information for the patient selected is displayed on the display apparatus 64.

By employing the above structure, the patient to whom the nursing care is intended is selected from the listing displayed on a display apparatus, so that the selection processing can be done with ease. Also, since the patient to whom a nursing care is to be conducted is selected from the listing displayed on the display apparatus, the selection processing can be performed with accuracy. Also, the screen used for the management of nursing care and the screen used to select a patient are switched around by pressing a button, so that the switching of the both screens can be made easily.

3. Preparation of Nursing Problems and Nursing Care Plans

Preparation of nursing problems/nursing care plans corresponds to Step 12 and Step 14 of FIG. 4. The problems to be resolved here may be expressed as follows. It is desired that the preparation of nursing problems be made with ease and the preparation of nursing problems be made with accuracy. Also, it is desired that nursing problems corresponding respectively to patients be prepared. It is desired that the preparation of a nursing care plan be made with ease. It is desired that the preparation of a nursing care plan be made with accuracy. It is desired that nursing care plans corresponding respectively to patients be prepared. To prepare the nursing problems/nursing care plans, the viewing preparation unit 44, the display apparatus 64, the operation apparatus 62, the input control unit 50, the control unit 42, the management unit 56, the recording unit 60, the problem preparation supporting unit 30, the first database 32, the plan preparation supporting unit 34 and the second database 36 are principally used here.

The problem preparation supporting unit 30 supports the preparation of nursing problem items for patients. To support the preparation of nursing problem items, the problem preparation supporting unit 30 uses nursing problem database contained in the first database 32. FIG. 8 illustrates a data structure of the nursing problem database contained in the first database 32. The nursing problem database includes a diagnosis-and-treatment department space 130, a disease space 132, a nursing problem space 134, and a nursing problem code space 136. The diagnosis-and-treatment department space 130 records a plurality of diagnosis and treatment departments for medical services in a hospital. The plurality of diagnosis and treatment departments include "gastroenterology" and "pediatrics", for example. The disease space 132 records a plurality of diseases, to be treated by departments, for a plurality of diagnosis-and-treatment departments, respectively.

For example, diseases such as esophagitis and colon cancer are recorded in correspondence to the diagnosis and treatment department which is gastroenterology (or department of digestive organs) here. The nursing problem space 134 records a plurality of kinds of items, to be included in the nursing problems, corresponding respectively to a plurality of diseases. For example, "there is a risk of suffering from a hemorrhagic shock due to hematemesis or melena" and the like are recorded in response to the colon cancer. As identifiers, nursing problem codes are assigned respectively to a plurality of kinds of items to be included in the nursing problems. The nursing problem code space 136 records the nursing problem codes corresponding respectively to a plurality of kinds of items to be included in the nursing problems. As described above, the diagnosis and treatment departments, the diseases and the nursing problem items are brought into correspondence with one another. That is, the nursing problem database defines a plurality of kinds of items, to be included in the nursing problems, across a plurality of diagnosis and treatment departments. Hereinafter, a "diagnosis and treatment department" will be referred to also or simply as "department".

Refer back to FIG. 2. The problem preparation supporting unit 30 presents a plurality of kinds of items to the nurse in a unified manner, by way of the viewing preparation unit 44 and the display apparatus 64. Further, the problem preparation supporting unit 30 has the nurse select a nursing problem item or items via the operation apparatus 62 and the input control unit 50. Here, "in a unified manner" corresponds to putting together and arranging a plurality of kinds of items by department and patient and also corresponds to integrating a plurality of kinds of items into a predetermined category or categories. More specific explanation is as follows. The problem preparation supporting unit 30 presents a plurality of departments to the nurse by way of the viewing preparation unit 44 and the display apparatus 64, and then receives from the nurse a specification as to the selection of a department.

The problem preparation supporting unit 30 extracts from the first database 32 a plurality of patient names corresponding to the department selected by the nurse. Then the problem preparation supporting unit 30 presents the plurality of extracted patient names to the nurse via the viewing preparation unit 44 and the display apparatus 64. Further, the problem preparation supporting unit 30 receives from the nurse a specification as to the selection of a disease name. The problem preparation supporting unit 30 extracts from the first database 32 a plurality of kinds of items corresponding to the selected disease name and then presents the plurality of extracted items to the nurse via the viewing preparation unit 44 and the display apparatus 64. Finally, the problem preparation supporting unit 30 receives a specification as to the selection of an item from the nurse via the operation apparatus 62 and the input control unit 50 and then extracts from the first database 32 a nursing problem code corresponding to the item selected by the nurse. As a result of the above processing, the problem preparation supporting unit 30 outputs the prepared nursing problem code to the plan preparation supporting unit 34.

As described above, the first database 32 stores a plurality of kinds of items to be included in nursing problems, as fixed phrases, respectively. And the problem preparation supporting unit 30 has the nurse select any of the fixed phrases. Further, the problem preparation supporting unit 30 presents an open-ended entry space to the nurse. This open-ended entry space corresponds to a space provided for giving a comment to a fixed phrase. There are cases where a nursing problem item for a patient is not determined uniquely, in which case the comment is entered. The management unit 56 associates the comment in the open-ended entry space entered by the nurse with the selected fixed phrase. The thus associated comment in the open-ended entry space together with the fixed phrase is stored in the recording unit 60. That is, they are stored in the nursing problem space 102 of FIG. 3.

Refer back to FIG. 2. The plan preparation supporting unit 34 supports the preparation of nursing care plans by searching through a nursing care plan database included in the second database 36 based on the nursing problem codes prepared for patients. Here, the nursing care plan database includes nursing care plan items which are brought into correspondence in advance with a plurality of kinds of items to be included in the nursing problem, respectively. FIG. 9 illustrates a data structure of the nursing care plan database included in the second database 36. The nursing care plan database includes a nursing problem code space 140, a target space 142, and a plan space 144. The nursing problem code space 140 records nursing problem codes corresponding respectively to a plurality of items included in the nursing problem. The target space 142 records targets or objectives corresponding respectively to the nursing problem codes. For example, a statement like "Find the bleeding in early stages and prevent a critical shock state" is recorded as a target or objection. Also, it can be said that the targets and plans correspond to the nursing problem codes. The plans are classified into OP, CP and EP as described above.

As described above, the second database 36 stores nursing care plan items as fixed phrases, respectively. And the plan preparation supporting unit 34 has any of the fixed phrases selected according to the nursing problem code selected in the problem preparation supporting unit 30. Further, the plan preparation supporting unit 34 presents an open-ended entry space to the nurse. This open-ended entry space corresponds to a space provided for giving a comment to a fixed phrase. There are cases where a nursing problem item for a patient is not determined uniquely, in which case the comment is entered. The management unit 56 associates the comment in the open-ended entry space entered by the nurse with the selected fixed phrase. The thus associated comment in the open-ended entry space together with the fixed phrase is stored in the recording unit 60. That is, they are stored in the nursing care plan space 104 of FIG. 3.

Refer back to FIG. 2. The viewing preparation unit 44 displays GUIs to be presented respectively for the problem preparation supporting unit 30, the plan preparation supporting unit 34 and the display of implementation results and evaluations described later, on the screen of the display apparatus 64. Hereinafter, the GUI to be presented for the problem preparation supporting unit 30 will be called a "problem list"; the GUI to be presented for the plan preparation supporting unit 34 will be called a "nursing care plan"; and the GUI to be presented for the display of implementation results and evaluations will be called a "nursing record". Here, the management unit 56 operates to perform the "nursing record". The communication unit 52, the input control unit 50 and the operation apparatus 62 are used for the entry of the nursing records. The viewing preparation unit 44 is so structured that the problem list, the nursing care plan and the nursing record are all displayed within a single screen. That is, provided is a screen such that the nursing problem, the nursing care plan, the nursing result and the evaluation can be read through by the nurse.

The viewing preparation unit 44 has a GUI, to be presented for the display of evaluations in the nursing record, displayed on a part of area where a GUI to be presented for the display of implementation results is displayed. That is, presented is a screen where the correspondence between an implementation result and an evaluation is clarified. Further, the evaluation also contains information on the current status of a patient, and an area for displaying a GUI to be presented for the display of an evaluation is provided in a manner that it is divided by an area corresponding to information on a patient condition and an area corresponding to an evaluation to information other than the information on a patient condition.

Here, the evaluation corresponds to a "SOAP format" which is one of recording modes for recording a process or progress. "S (subjective)" corresponds to subjective actions or appeals by patients, which are, for example, direct remarks by patients regarding nursing problems or those according thereto. That is, S may be said to represent subjective information about patients. For example, S is "want to have the body wiped" or "change into pajamas". "O (objective)" corresponds to numerical values such as laboratory results and vitals or contents based on an objective observation by a nurse and experiments. That is, O may be said to represent objective information about patients. For example, O is "at a doctor's round visit, a lower limb/upper limb and a precordial region were not wiped and consequently the skin is a bit sticky" or "cleanliness activity cannot be conducted by his/her own ability and thus he/she cannot change the clothes by himself/herself because of paralysis in left upper and lower limbs together with movement restrictions as a result of a treatment".

"A (assessment)" corresponds to nurses' judgment to S or O or thought processes. That is, A may be said to represent an evaluation by a nurse. For example, A is "with skin contamination/moistness left unattended, a risk of occurrence of decubitus increases". "P (plan)" corresponds to a future schedule or plan based on A. For example, P is "(1) Perform a bed bath of a lower limb/upper limb and a precordial region; (2) Observe the skin condition; and (3) Change underwear/nightwear after the bed bath". The information on a patient condition corresponds to S and O in the SOAP format, whereas an evaluation to information other than the information on a patient condition corresponds to A and P in the SOA format.

In cooperation with the operation of the problem preparation supporting unit 30, the viewing preparation unit 44 defines, on a screen, a first area where a plurality of departments are to be displayed, a second area where a plurality of patients are to be displayed, and a third area where a plurality of kinds of items to be included in a nursing problem are to be displayed. The first to the third area are not overlapped with one another on the screen, and the size, position and the like of each area may be arbitrary. To clarify the correspondence among departments, diseases and items, the first to the third area may be arranged adjacent to each other. The viewing preparation unit 44 displays a plurality of departments in the first area. When any of a plurality of departments displayed in the first area is selected by a nurse via the operation apparatus 62, the viewing preparation unit 44 displays a plurality of patients associated with the selected department, in the second area. When any of the plurality of patients displayed in the second area is selected by the nurse, the viewing preparation unit 44 displays a plurality of kinds of items associated with the selected patient, in the third area.

In cooperation with the plan preparation supporting unit 34, the viewing preparation unit 44 displays information in the nursing care plan displayed on the screen. That is, after the plan preparation supporting unit 34 conducts a search through the second database 36 based on nursing problem items prepared for patients, the viewing preparation unit 44 displays search results in the area allotted to the nursing care plan.

Figure 10:
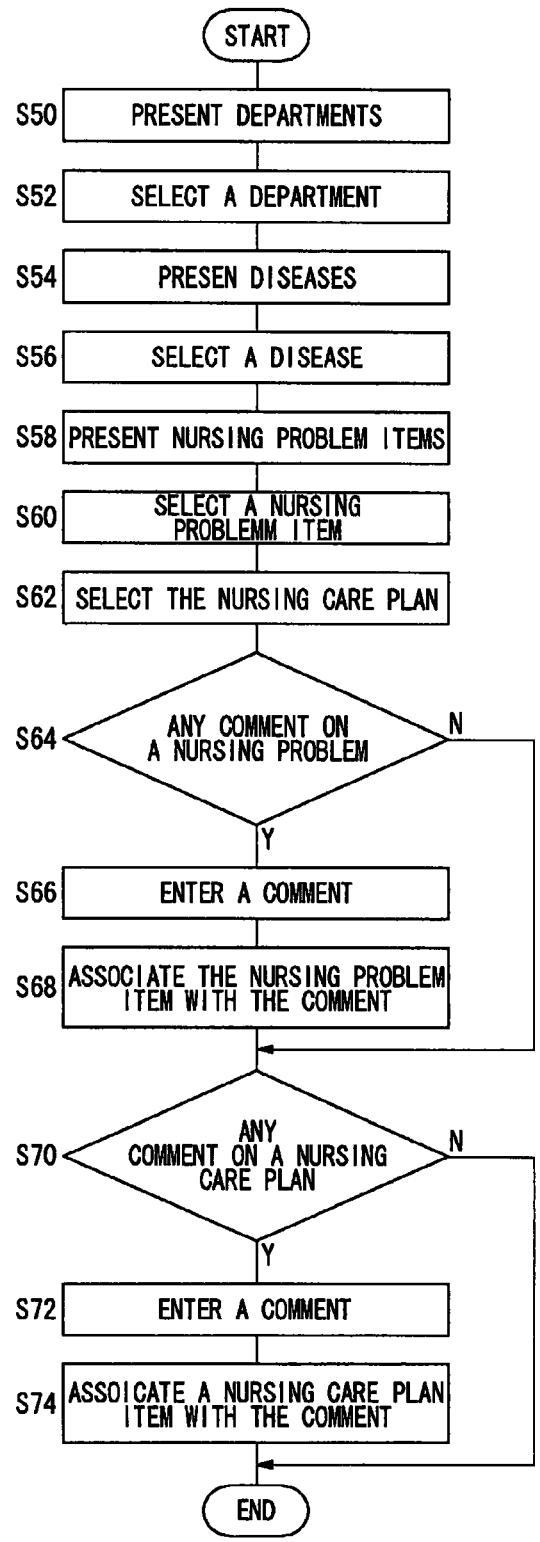
FIG. 10 is a flowchart showing a procedure for preparing nursing problems and nursing care plans in a PC of FIG. 2.
Figure 11:
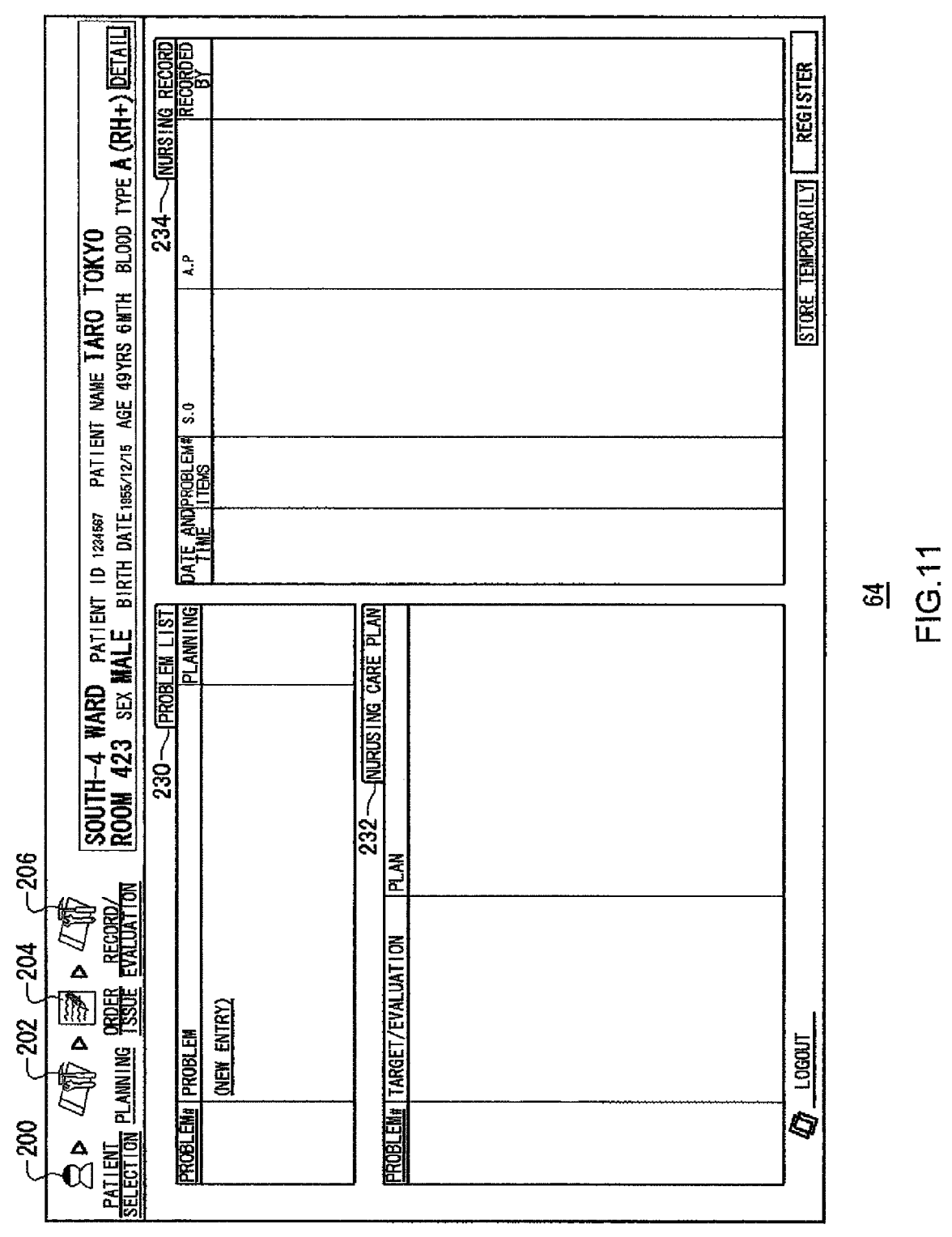

FIG. 10 is a flowchart showing a procedure for preparing nursing problems and nursing care plans in the PC 20. The viewing preparation unit 44 has the display apparatus 64 display an initial screen. FIG. 11 illustrates an initial screen, at a planning stage, displayed on the display apparatus 64. Similar to FIG. 7, a patient selection button 200 to a recording/evaluation button 206 are displayed but the planning button 202 is selected here. Also, a problem list space 230, a nursing plan space 232, a nursing record space 234 are displayed on the screen, and these correspond to a problem list, a nursing care plan and a nursing record, respectively. As shown in FIG. 11, the problem list, the nursing care plan and the nursing record are so arranged as to be read through. Refer back to FIG. 10. The problem preparation supporting unit 30 presents a plurality of departments in the display apparatus 64 (S50). A department is selected by the nurse via the operation apparatus 62 (S52).

Figure 12:
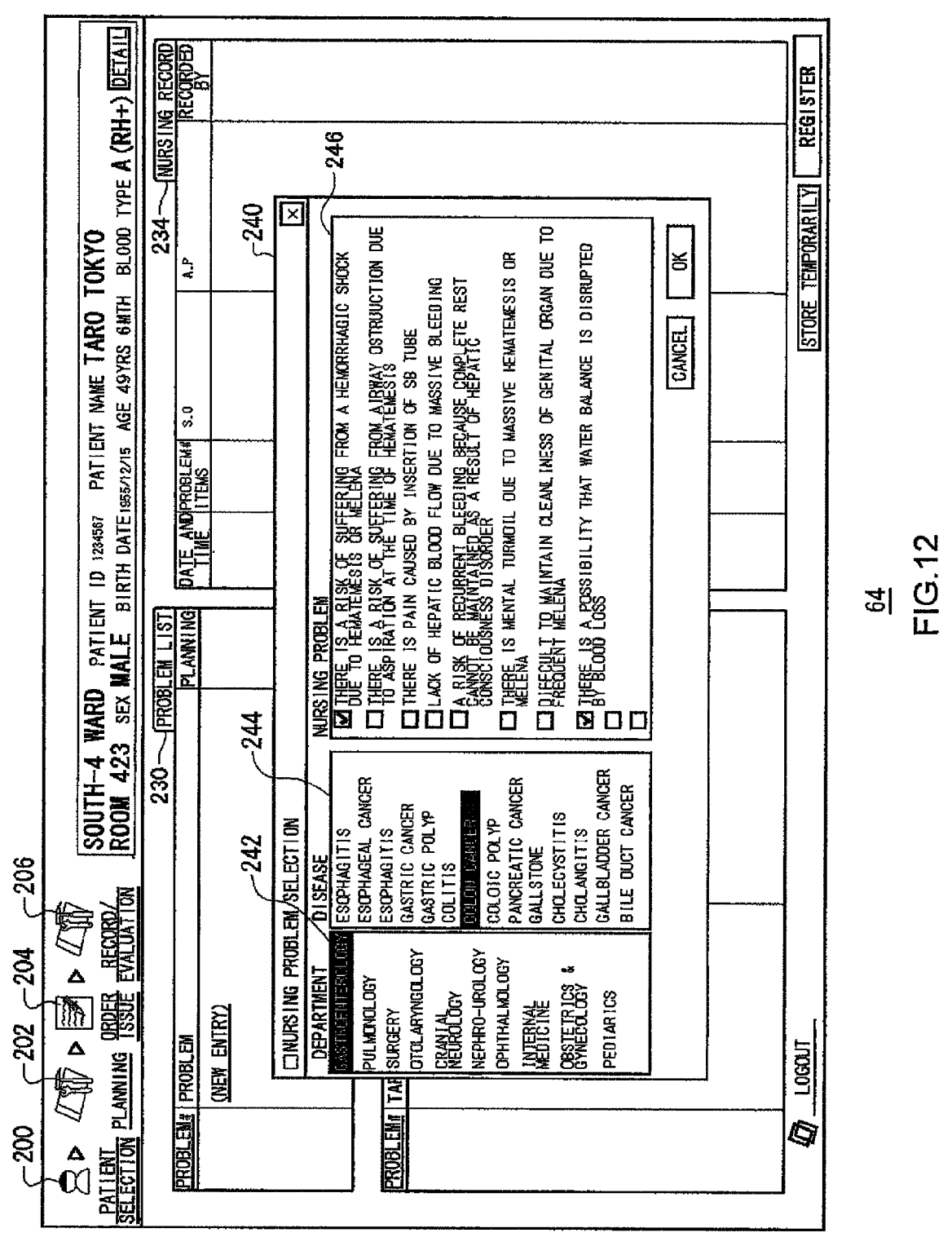

Consequently, the problem preparation supporting unit 30 presents a plurality of patients to the display apparatus 64 (S54). A patient is selected by a nurse using the operation apparatus 62 (S56). Further, the problem preparation supporting unit 30 presents to the display apparatus 64 a plurality of kinds of items for the nursing problems (S58). An item or items are selected by the nurse via the operation apparatus 62 (S60). FIG. 12 illustrates a screen for the nursing problem selection displayed on the display apparatus 64. A nursing problem selection window 240 is displayed in the center of the screen. The nursing problem selection window 240 contains a department space 242, a disease space 244 and a nursing problem space 246, which correspond respectively to the above-described first to third areas.

FIG. 12 corresponds to Step 60 of FIG. 10. In the example shown in FIG. 12, "gastroenterology" was already selected in the department space 242 and "colon cancer" was already selected in the disease space 244. Any of the nursing problem selection window 240 is already selected in FIG. 12. At the stage of Step 50, nothing is displayed in the disease space 244 and the nursing problem space 246. That is, once an option is selected, a subsequent option is displayed.

Figure 13:
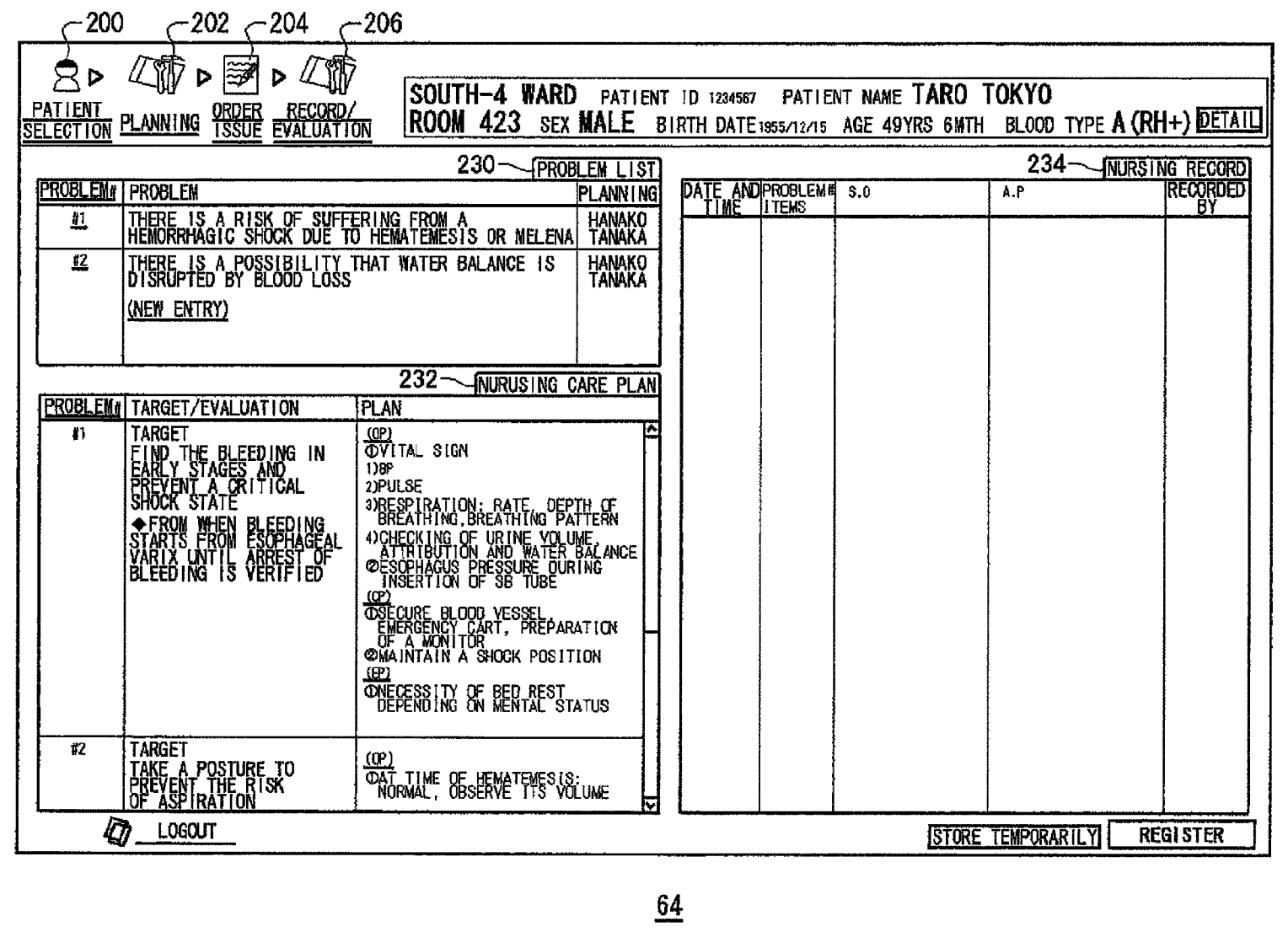

Refer back to FIG. 10. When a nursing problem item is selected, the plan preparation supporting unit 34 selects the nursing care plan while conducting a search through the second database 36 (S62). FIG. 13 illustrates a screen displayed after a nursing care plan displayed on the display apparatus 64 has been entered. Nursing problem items are displayed in the problem list space 230, and nursing care plan items are displayed in the nursing care space 232. Here, "#1" and so forth correspond to the identifiers used to identify a set of items that are brought into correspondence with one another among the nursing items included in the nursing care plan, the implementation results and the evaluations. Refer back to FIG. 10. The management unit 56 prompts the entry of a comment on the nursing problem; and if there is a comment to the nursing problem (Y of S64), the nurse will enter the comment using the operation apparatus 62 (S66).

Figure 14:
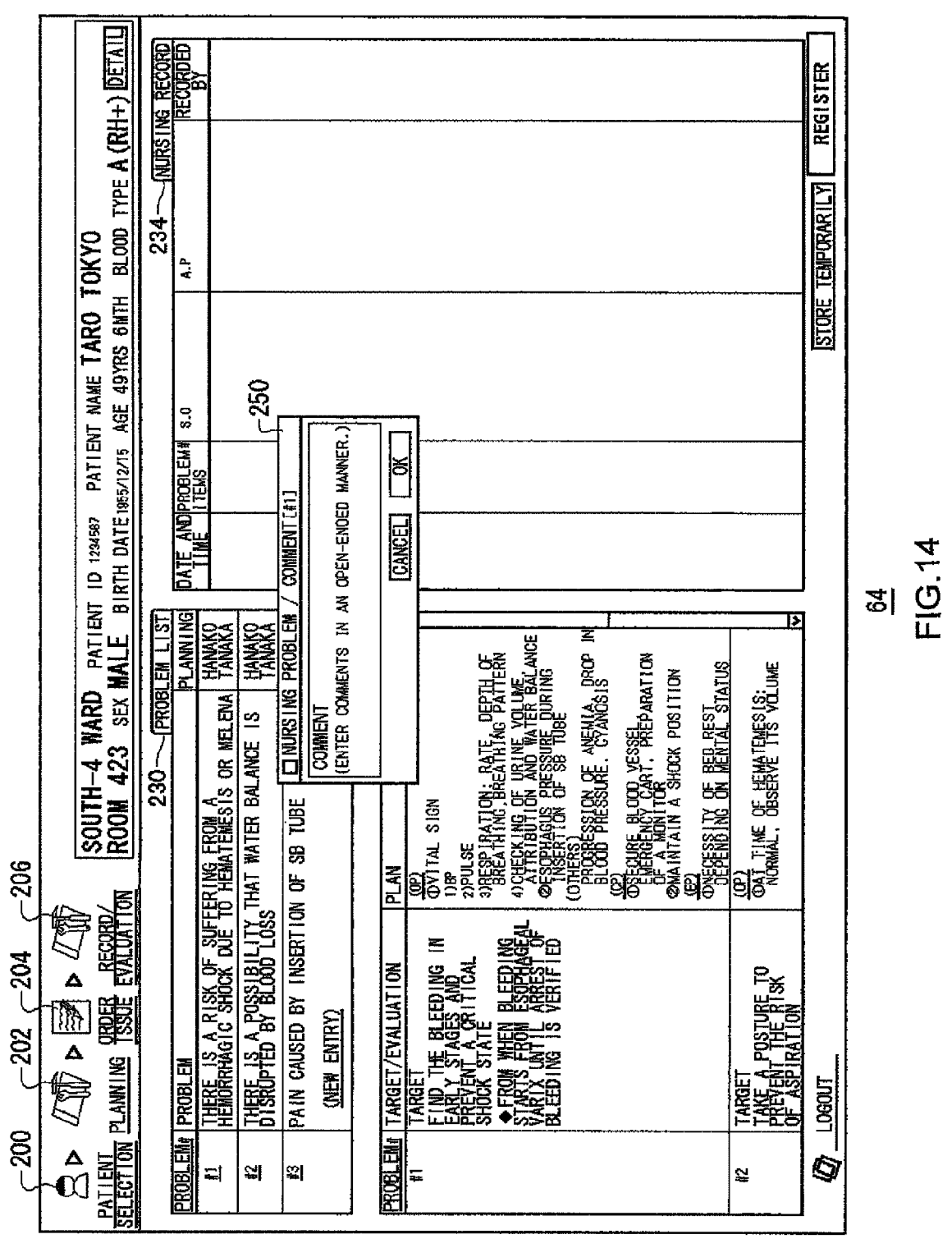
Figure 15:
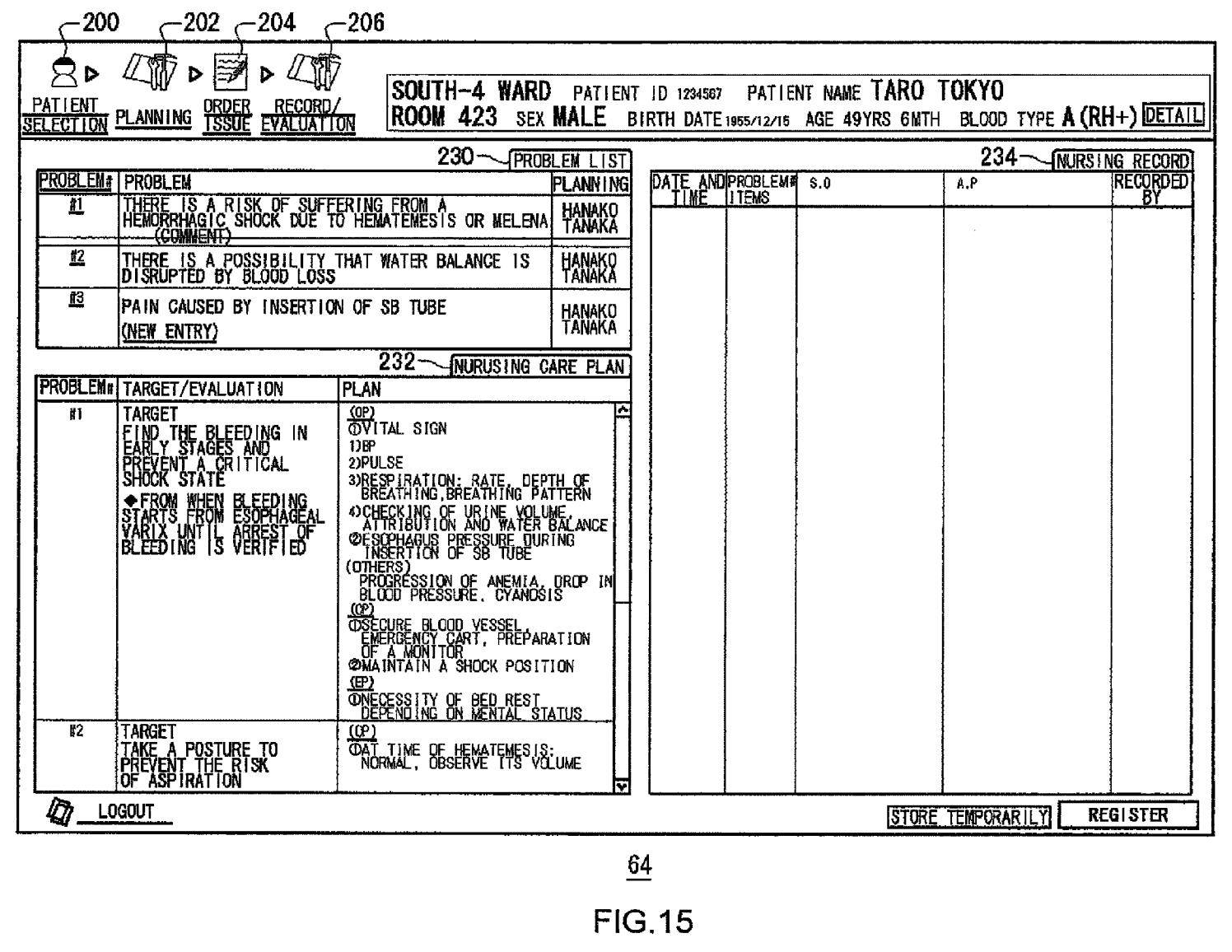

The management unit 56 associates nursing problem items with the comment (S68) and then records them in the recording unit 60. If there is no comment on a nursing problem (N of S64), such processing will not be performed. FIG. 14 illustrates an additional window for a comment on the nursing problem displayed on the display apparatus 64. A nursing problem open-ended entry window 250 is displayed in the center part of a screen. The nurse enters a comment into the nursing problem open-ended entry window 250. FIG. 15 illustrates a screen displayed after the comment on the nursing problem displayed on the display apparatus 64 has been entered. The comment is entered in the space provided for the problem "#1" in the problem list space 230.

Figure 16:
FIG. 16 illustrates an edit screen of a nursing care plan displayed on a display apparatus of FIG. 2.
Figure 17:
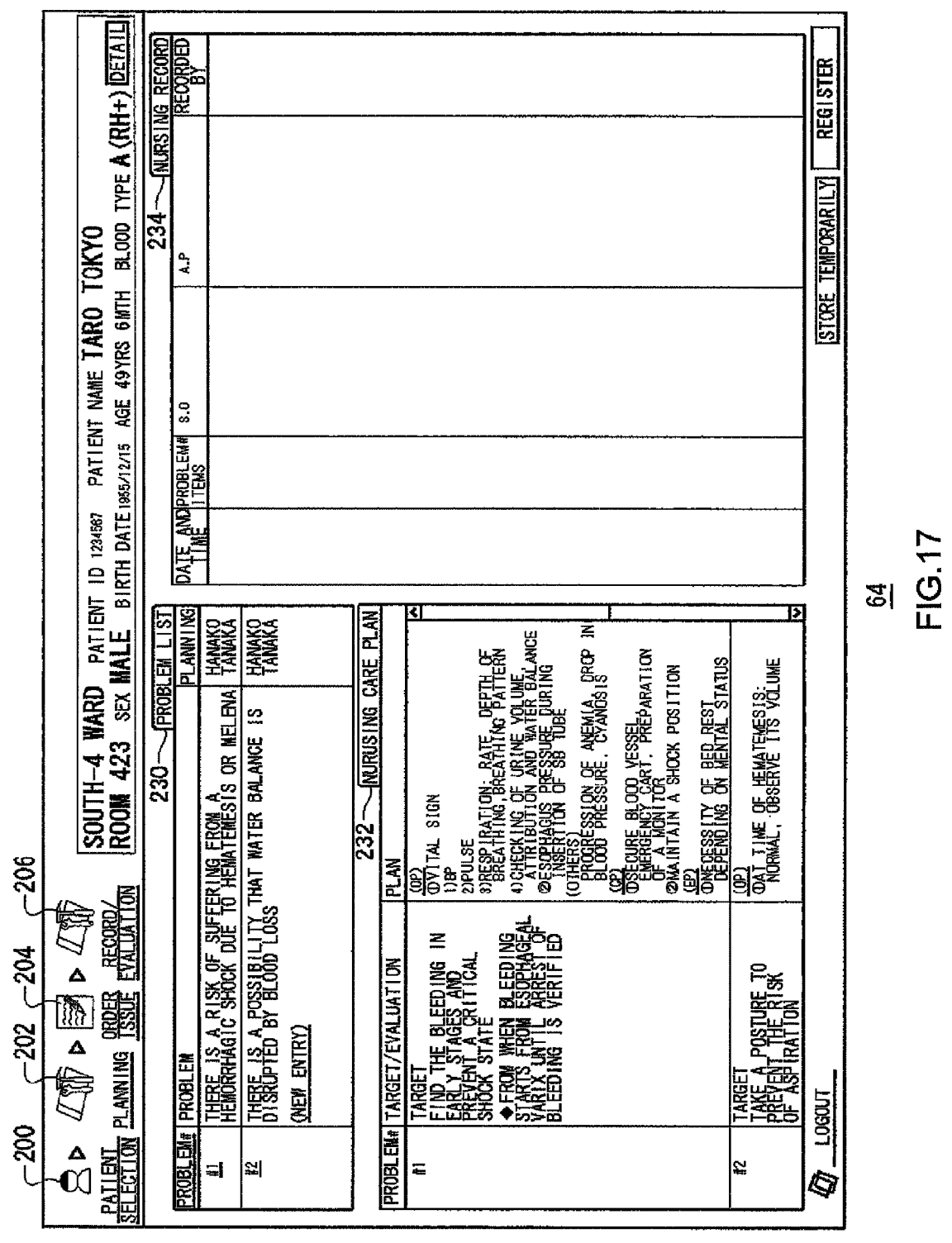

Refer back to FIG. 10. If there is any comment on a nursing care plan (Y of S70), the nurse will enter the comment using the operation apparatus 62 (S72). The management unit 56 associates nursing plan items with the comment (S74) and then records them in the recording unit 60. If there is no comment on a nursing care plan (N of S70), such processing will not be performed. FIG. 16 illustrates an additional window for a comment on the nursing problem displayed on the display apparatus 64. A nursing care plan edit window 260 is displayed in the center part of a screen. The nursing care plan edit window 260 includes a typical statement space 262 and an open-ended entry space 264. The nurse edits the already entered nursing care plan items by entering a predetermined specification to the typical statement space 262. Also, the nurse enters a comment into the open-ended entry space 264. FIG. 17 illustrates a screen displayed after the nursing care plan displayed on the display apparatus 64 has been edited. The comment is entered in the plan for "#1" in the nursing care plan space 232.

An operation of the PC 20 structured as above will now be described. From among a plurality of kinds of items to be included in the nursing problem displayed on the display apparatus 64, the nurse selects via the operation apparatus 62 a nursing problem item or items which is/are to fall under the relevant category. The PC 20 selects a nursing care plan or plans corresponding to the selected nursing problem item or items, and displays it on the display apparatus 64. The nurse enters a comment to the nursing problem and a comment to the nursing care plan using the operation apparatus 62. The PC 20 records the prepared nursing problem items, the nursing care items and the comments thereto by bringing them into correspondence with one another.

By employing the above-described structure, when the nursing problems are to be prepared, selection is made from predefined items, thus making the preparation of nursing problems easier. Mistakes made in the preparation of nursing problems can be reduced. The nursing problems are defined through a plurality of stages. Thus, if one of the plurality of stages is selected, the candidates for the selection for the next stage will be displayed. As a result, the selection processing becomes clear and mistakes made in the selection can be reduced. Since a plurality of stages are so arranged as to be positioned adjacent to one another on a single screen, the correspondence therebetween can be clarified. When the nursing problems are to be prepared, not only the predefined items but also comments may be added, so that the nursing problems suited respectively for patients can be prepared.

Since a nursing care plan item is selected from among the nursing problem items by referring to a database where the nursing problem items and the nursing care plans are brought into correspondence with each other, the nursing care plan can be prepared with ease. Since the nursing care plans are defined beforehand, mistakes made in the preparation of the nursing care plans can be reduced. When the nursing care plans are to be prepared, not only the predefined items but also comments may be added, so that the nursing care plans suited respectively for patients can be prepared. Since nursing problems, nursing care plans, implementation results and evaluations are arranged on a single screen, the relationship among them can be clarified. Since the correspondence among them is clarified, the accuracy in conducting the nursing actions can be enhanced. Since the evaluation is displayed in a part of area where the implementation result is to be displayed, the relationship between the implementation result and the evaluation can be clarified. Since the information on the current status of a patient and other evaluations are displayed in an area where the evaluation is to be displayed in a manner that they are brought into correspondence with each other, the relationship therebetween can be clarified.

4. Oder Issuance

The issuing of orders corresponds to Step 16 of FIG. 4. Here the problems to be resolved here may be indicated as follows. It is desired that mistakes in the preparation of order be minimized. It is desired that the processing amount for the issuing of orders be reduced. It is also desired that the mistakes made in conducting the nursing actions be reduced.

A description is given of the order issuance before describing a specific structure thereof. FIG. 18 is a schematic view showing an order issuance processing in the nursing information management system 10. FIG. 18 illustrates a case where an order for injection is issued as an order issuance. The nurse prepares an order (S80) and registers the order (S82). In the case of injection, when the order has been registered, the processing branches out into the following processings. A first processing specifies to a not-shown ward system the reception of a specification in the ward (S84). The reception of a specification is done by the nurse. A second processing specifies for a not-shown pharmaceutical division system to dispense and pay out medicines (S86). The dispensing and paying out of medicines is done by a pharmacist.

A third processing specifies to a not-shown ward system the mixed injection of medicines in the ward (S88). The mixed injection is also called "mixing". The mixed injection is performed by the nurse. A fourth processing specifies to the nursing information management system 10 the start of injection to a patient in the ward (S90). A fifth processing specifies to the nursing information management system 10 the termination of injection to a patient in the ward (S92). The injection is performed by the nurse. Here, the injection includes both intravenous injection by drip and one-shot injection. In the case of intravenous injection by drip, the administration is done spending a long duration of time, so that a work for the start of the dosing treatment and a work for the termination thereof generally differ from each other. In the case of one-shot injection, the dosing treatment can be terminated in a single action, so that the start of the dosing treatment and the termination thereof are done almost simultaneously.

To issue orders, the viewing preparation unit 44, the display apparatus 64, the operation apparatus 62, the input control unit 50, the control unit 42, the management unit 56, the recording unit 60, the specification unit 38, the third database 40 and the communication unit 52 in FIG. 2 are principally used.

Figures 19, 20:
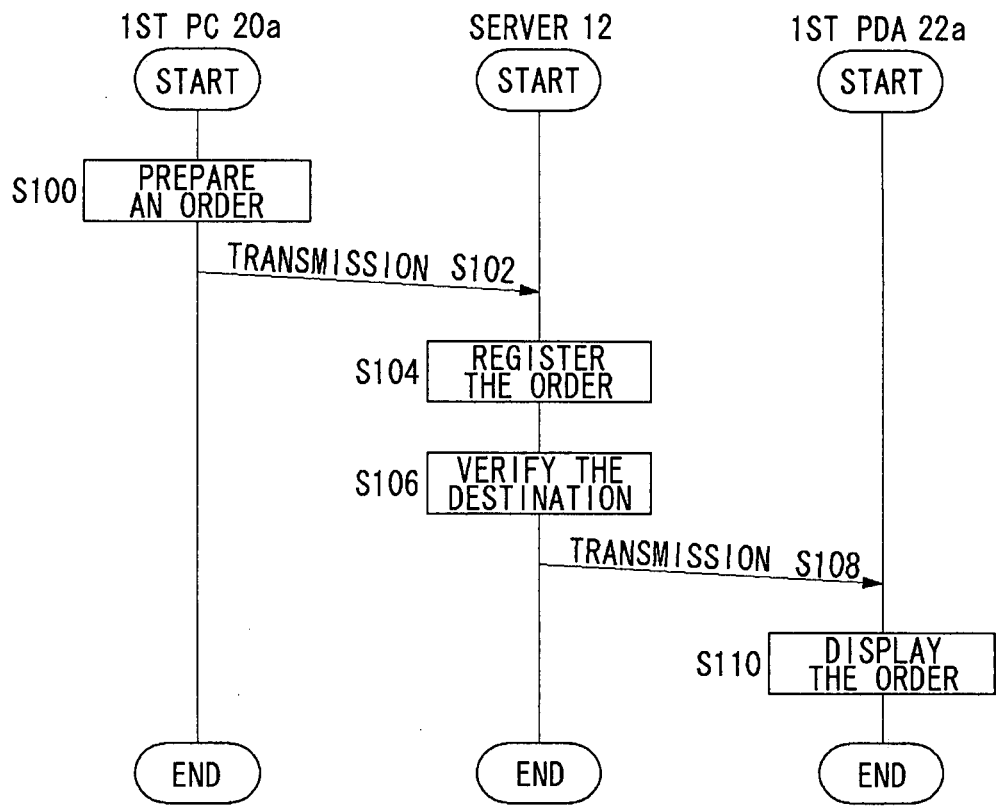
FIG. 19 illustrates a data structure of a database for use in orders included in a third database of FIG. 2.
FIG. 20 is a sequence diagram showing a procedure for processing the issuance of orders in a nursing information management system of FIG. 1.

The specification unit 38 supports the generation of orders for a specification, based on the nursing items, in an area of screen displayed by the viewing preparation unit 44. For the purpose of supporting the generation of orders, the specification unit 38 uses a database for use in orders included in the third database 40. FIG. 19 illustrates a data structure of the order database included in the third database 40. The database for use in orders includes an item type space 150, a classification space 152 and an order item space 154. The database for use in order is defined in a manner such that a plurality of classifications defined in the classification space 152 are associated respectively with those in the item type space 150 and a plurality of order items defined in the order item space 154 are associated respectively with those in the classification space 152.

The item type space 150 defines the type of an order. Here, the types of orders include "observation", "care", "guidance", "supervisory measures", "others" and "reservation". The classification space 152 defines the classification of diseases. Here, the classification of diseases includes "gastrointestinal disease", "cardiovascular disease" and so forth. The order item space 154 defines the contents of orders. Here, the contents of orders include "nausea", "vomiting" and so forth. Such a database for use in orders is displayed on the display apparatus 64 by the viewing preparation unit 44, and the nurse selects a predetermined item or items from the database for use in orders by referring to the nursing items. For instance, if the nursing items relate to a gastrointestinal disease, the nurse will select a gastrointestinal disease from the classification space 152.

Refer back to FIG. 2, the above-described selection by the nurse is received by the operation apparatus 62 and the input control unit 50. The orders generated are recorded in the recording unit 60. The specification unit 38 displays, on the display apparatus 64, the contents indicating that the generated orders shall be transmitted. Thereafter, if the specification unit 38 receives a confirmed operation from the nurse via the operation apparatus 62, the specification unit 38 will output the orders to the communication unit 52. The orders are also sent to the PDA 22 via the server 12.

FIG. 20 is a sequence diagram showing a procedure for processing the issuance of orders in the nursing information management system 10. The nurse prepares orders in the first PC 20a (S100). Based on the specification of the order issuance by the nurse, the first PC 20a transmits the prepared orders to the server 12 (S102). The server 12 registers the orders (S104). Also, the server 12 verifies the destinations to which the registered order are to be transmitted (S106). As a result, suppose that the destination is the first PDA 22a. Then, the server 12 sends the registered order to the first PDA 22a (S108). The first PDA 22a displays the received order on a not-shown display (S110).

Figure 21:
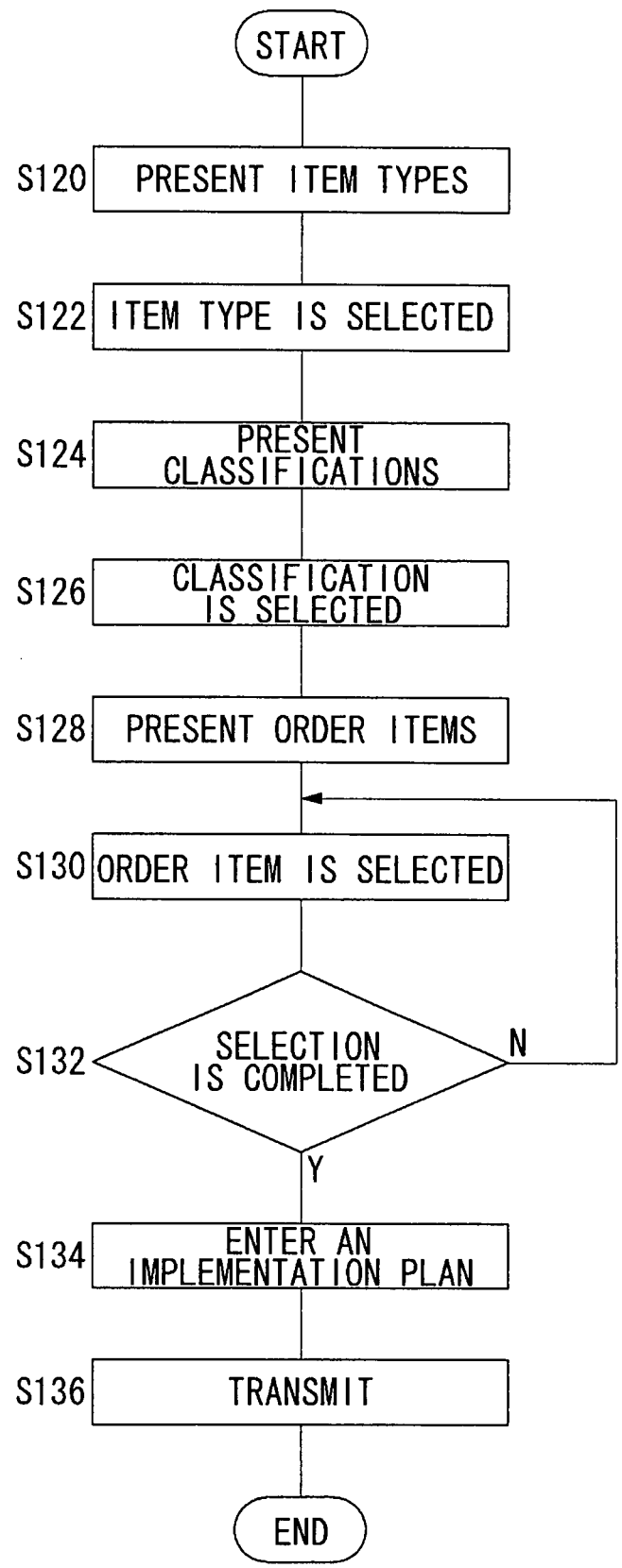
FIG. 21 is a flowchart showing a procedure for processing the issuance of orders in a PC of FIG. 2.

FIG. 21 is a flowchart showing a procedure for processing the issuance of orders in the PC 20. The specification unit 38 has the display apparatus 64 present the item types, by referring to the third database 40 (S120). A item type is selected by the nurse via the operation apparatus 62 (S122). The specification unit 38 receives a specification of the selection. The specification unit 38 has the display apparatus 64 present the classifications, by referring to the third data base 40 (S124). A classification is selected by the nurse via the operation apparatus 62 (S126). The specification unit 38 receives a specification of the selection. The specification unit 38 has the display apparatus 64 present the order items, by referring to the third database 40 (S128). An order item is selected by the nurse via the operation apparatus 62 (S130).

Figure 22:
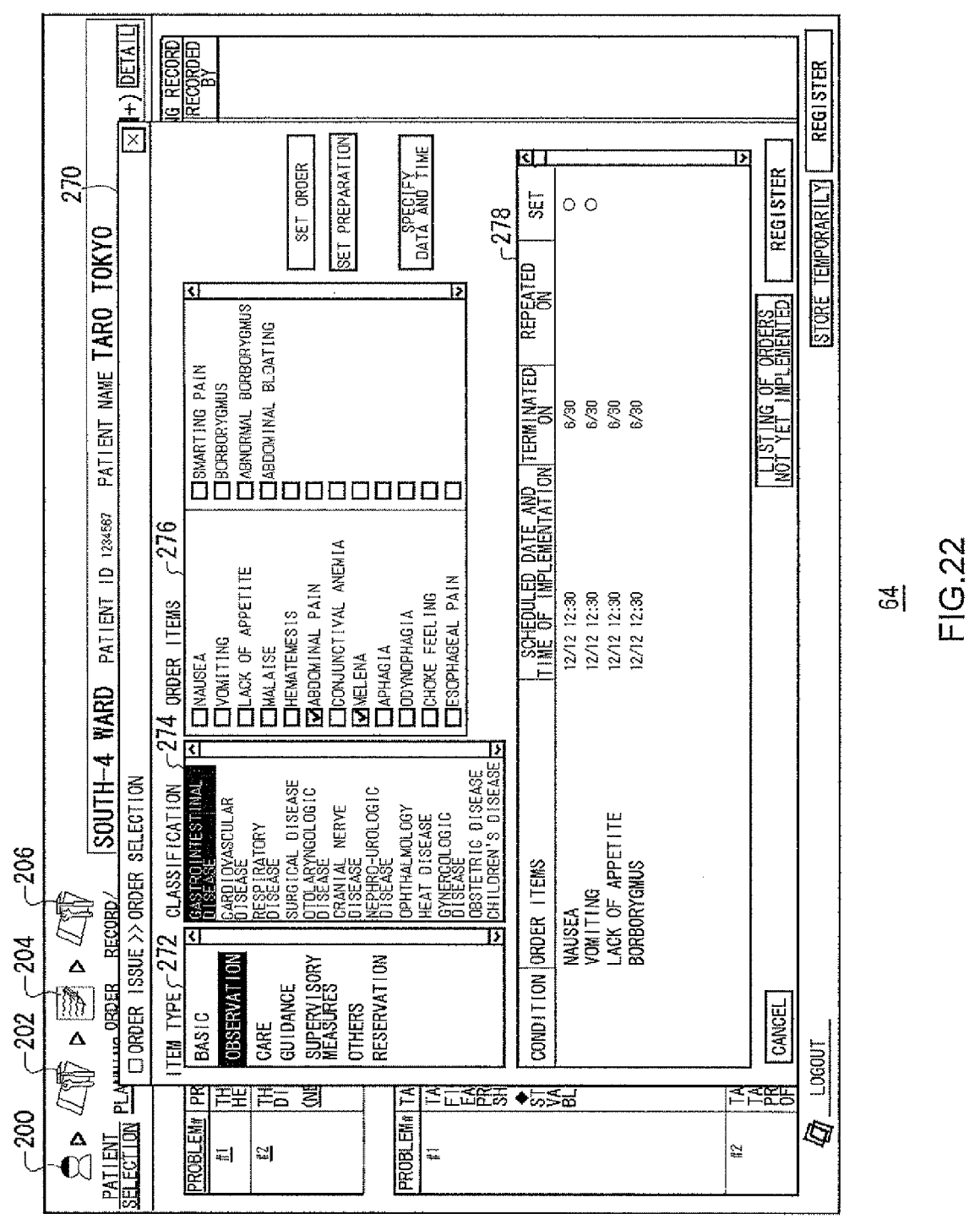

The specification unit 38 receives a specification of the selection. If the selection of an order item has not been completed (N of S132), the processing of Step 130 is repeated. If, on the other hand, the selection of an order item has been completed (Y of S132), the nurse enters a plan for implementation using the operation apparatus 62 (S134). The specification unit 38 receives the entered plan for implementation. FIG. 22 illustrates a screen displayed on the display apparatus 64 at a stage of order issuing. FIG. 22 corresponds to Step 134 of FIG. 21. Though the patient selection button 200 to the record/evaluation button 206 are displayed in FIG. 22, the order issue button 204 is selected this time. An order issue window 270 is displayed in the center of the screen. The order issue window 270 includes an item type space 272, a classification space 274, an order item space 276 and a plan space 278. The item type space 272, the classification space 274 and the order item space 276 correspond respectively to the item type space 150, the classification space 152 and the order item space 154 of FIG. 19.

The plan space 278 corresponds to a plan for implementation. Here, if at a stage of selecting any from the item type space 272 the contents of the classification space 274 and the order item space 276 are not displayed and any from the item type space 272 is selected, the contents of the classification space 274 will be displayed. That is, if the selection is made at a predetermined option in the order of the item type space 272, the classification space 274 and the order item space 276, options following them are displayed. Refer back to FIG. 21. The specification unit 38 combines the selected item type, classification, order item and plan for implementation so as to turn them into an order. As the specification unit 38 receives a specification of the order via the operation apparatus 62 from the nurse, the communication unit 52 transmits the order to the server 12 (S136).

An operation of the nursing information management system 10 structured as above is now described. Using the operation apparatus 62, the nurse prepares orders by referring to the nursing items displayed on the display apparatus 64. If the prepared order is fine, the nurse enters, using the operation apparatus 62, a check indicating that the order has been verified. The PC 20 sends the order to the server 12. The order is also sent to the PDA 22.

By employing the above-described structure, the nurse prepares the orders by referring to a nursing care plan displayed on the screen. Thus the occurrence of mistakes in the preparation of orders can be reduced. Also, the transmission of the prepared orders achieves the registration of them in the server, thus unifying the preparation of orders and the registration thereof. Since the preparation of orders and the registration thereof can be unified, the processing load in the issuance of orders can be reduced. If the orders are transmitted to a server corresponding to other systems, the issuance of orders can be integrated with other systems. Since verification by the nurse is done at the time of sending the order, a prepared order containing any error can be corrected. Since the transmitted order is sent to the PDA carried by the nurse, the nurse can verify the contents of the order through his/her PDA. Also, the occurrence of mistakes in conducting nursing actions can be reduced.

5. The Recording and Displaying of Implementation Results

The recording and displaying of implementation results corresponds to Step 20 of FIG. 4. The problems to be resolved here may be expressed as follows. It is desired that when displaying the implementation results, the listing of the implementation results be displayed even though a display area available is limited. It is desired that the verification required by a nurse be made with ease. To record and display the implementation results, the viewing preparation unit 44, the display apparatus 64, the control unit 42, the management unit 56, the recording unit 60, the communication unit 52, the storage 48 and the selector 46 are principally used here. It is assumed that the nurse performs a nursing care action in Step 18 of FIG. 4. The nurse enters the implementation results of the nursing care actions into the PDA 22. The PDA 22 transmits the received implementation results to the PC 20.

The communication unit 52 receives the implementation results of the nursing items for patients. The received implementation results may be a result for a single nursing item or that for a plurality of nursing items. In the latter case, the implementation result includes body temperature and urine volume, for example. As information attached to or accompanied by the implementation result, the communication unit 52 receives also information on a person, who has performed a nursing care action, and time at which the nursing care action was implemented (hereinafter this information will be referred to as "added information"). The communication unit 52 outputs the received implementation result and the added information to the recording unit 60. The recording unit 60 records the inputted implementation results and the added information.

The storage 48 stores, in advance, predetermined conditions used in the selection unit 46. Though the details will be discussed later, the selector 46 selects at least part of implementation results recorded in the recording unit 60, and displays the selected implementation result on the display apparatus 64. The storage 48 stores conditions that serve as criteria for the selection in the selector 46. Now, if there are a plurality of kinds of implementation results in the implementation results in the recording unit 60, the storage 48 stores conditions corresponding respectively to the plurality of kinds of nursing items. For instance, those conditions are a condition for temperature and a condition for urine volume, which are conditions for a nursing item to be displayed on the display apparatus 64. The storage 48 defines a condition for the discrepancy between the implementation result recorded in the past and that recorded anew. The implementation result recorded in the past is, for example, one recorded last time. For instance, that there is a variation of ±1° C. from the body temperature recorded last time is defined as a condition for body temperature. Also, a definite value may be defined as a condition. For instance, a condition for body temperature is set as being higher than 37° C.

Figure 23:
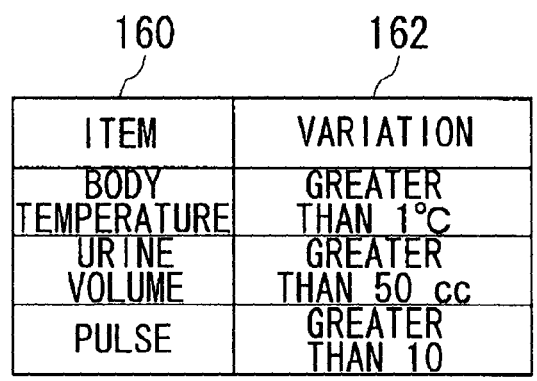
FIG. 23 shows conditions stored in a storage of FIG. 2.

FIG. 23 shows conditions stored in the storage 48. The conditions include an item space 160 and a variation space 162. Here, that the variation from the last time is "greater than 1° C." is set as a condition for "body temperature". That the variation from the last time is "greater than 50 cc" is set as a condition for "urine volume". That the variation from the last time is "greater than 10" is set as a condition for "pulse". Refer back to FIG. 2. The operation apparatus 62 receives a specification of changes in the conditions stored, from the nurse via the operation apparatus 62. Further, the storage 48 updates the condition by the specification received.

From among the implementation results recorded in the recording unit 60, the selector 46 selects implementation results that satisfy a condition stored in the storage 48. As described above, the conditions stored in the storage 48 are defined for the discrepancies between the implementation results recorded in the past and the newly recorded implementation results. Hence, if a newly recorded implementation result satisfies the condition, the selector 46 will select the newly recorded implementation result. According to the above-described example, if the discrepancies between the newly recorded implementation results and those recorded last time become larger, the selector 46 will select the newly recorded implementation results. That is, the selector 46 selects an implementation result that exhibits a somehow large variation. This is because the nurse directs more attention to a case exhibiting a larger variation. The viewing preparation unit 44 has the listing of the implementation result selected by the selector 46 displayed on a partial area, allotted for displaying the listing, of the screen of the display apparatus 64. Since the implementation result to be displayed is selected, as many implementation results to be verified by the nurse as possible are displayed on the screen even if the area allotted on the screen is limited.

Figure 24:
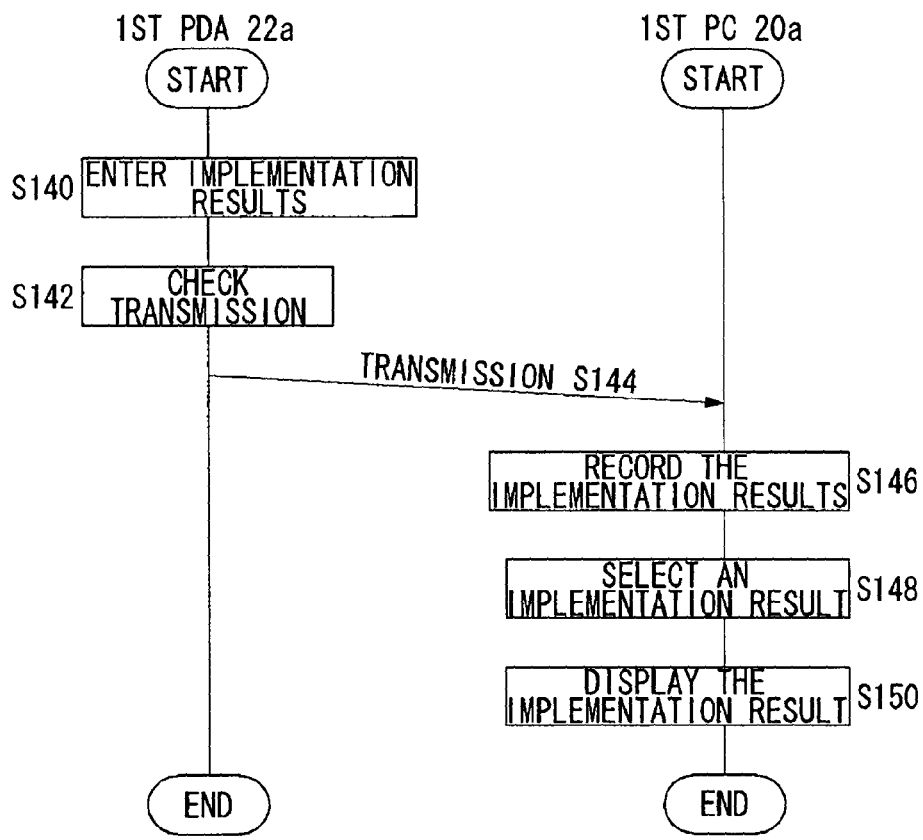
FIG. 24 is a sequence diagram showing a procedure for recording and displaying an implementation result in a nursing information management system of FIG. 1.

FIG. 24 is a sequence diagram showing a procedure for recording and displaying an implementation result in the nursing information management system 10. A nurse enters an implementation result of a nursing action into the first PDA 22a (S140). FIG. 25 illustrates an entry screen of the implementation result displayed by a PDA 22. FIG. 24 corresponds to a case when a measured body temperature is entered. FIG. 25 illustrates buttons through which numerals are entered onto the center part of the screen. The nurse taps on buttons corresponding to the values to be inputted, and enters values representing an implementation result. As the entry of values for the implementation results has been completed, the nurse taps on a "set" button. If there are any other implementation results to be entered, the first PDA 22a will switch the screen to the one for the entry thereof. Note that the first PDA 22a requests the entry of implementation results corresponding to nursing items. The nursing items has been conveyed to the first PDA 22a by the orders which had already been issued.

Refer back to FIG. 24. When the first PDA 22a receives an implementation result, it will prompt the nurse to check a transmission (S142). FIG. 26 illustrates a send screen for the implementation result displayed by the PDA 22. As contents to be sent to the screen, displayed are "body temperature", "urine volume" and "pulse", which are nursing items, and their respective measured values and measured time. If the contents of them are correct, the nurse will tap on a "send" button (S144). Refer back to FIG. 24. The first PDA 22a sends the implementation result to the first PC 20a. The first PC 20a records the implementation result (S146). Following this, the first PC 20a selects the implementation result (S148). Further, the first PC 20a displays the implementation result (S150).

Figure 27:
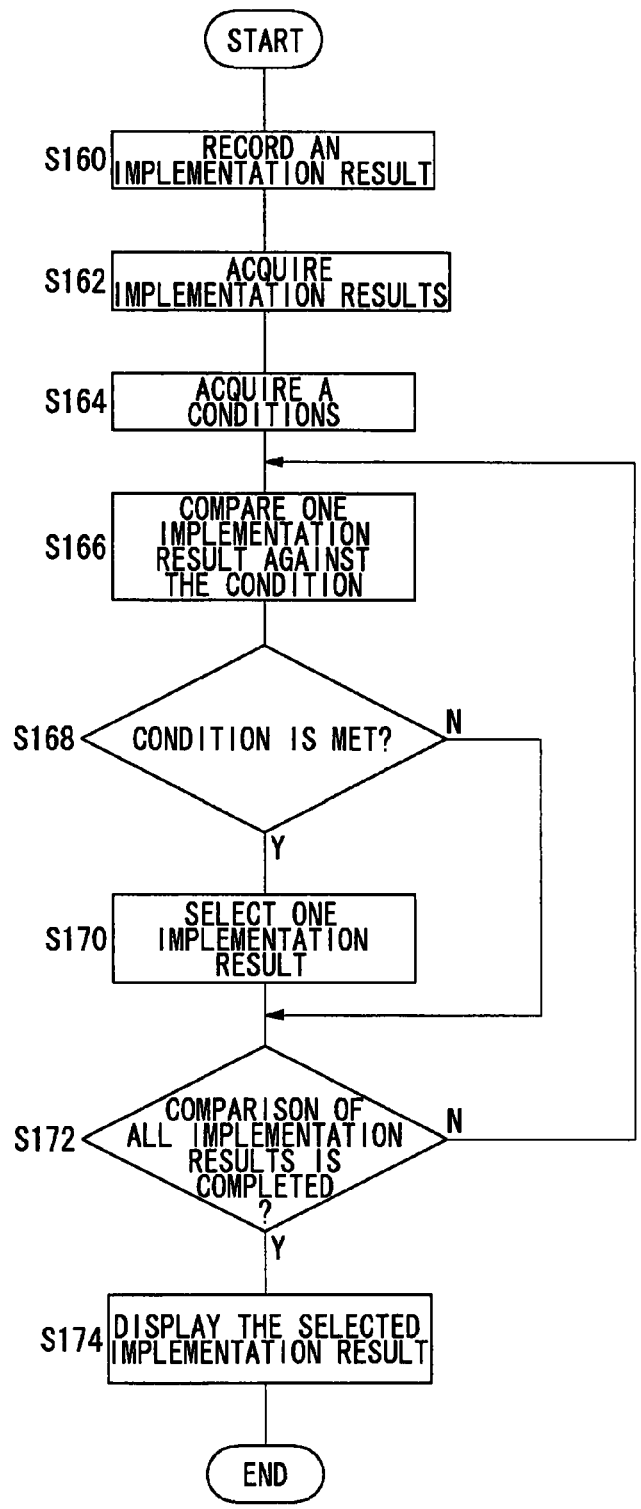
FIG. 27 is a flowchart showing a procedure for displaying an implementation result in a PC of FIG. 2.

FIG. 27 is a flowchart showing a procedure for displaying an implementation result in the PC 20. The recording unit 60 records the implementation result entered (S160). The selector 46 acquires implementation results from the recording unit 60 (S162) and acquires a condition from the storage 48 (S164). If there are a plurality of kinds of implementation results, the selector 46 will compare one of the implementation results against the condition (S166). If one of the implementation results satisfies the condition (Y of S168), the selector 46 will select the one of the implementation results (S170). If, on the other hand, one of the implementation results does not satisfy the condition (N of S168), no selection processing will be performed. If the comparing of all of the implementation results against the condition has not been completed (N of S172), the selector 46 will repeat the processing of Step 166.

Figure 28:
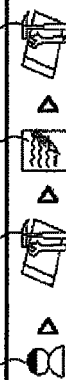
FIG. 28 illustrates an initial screen, at a stage of recording/evaluation, displayed on a display apparatus of FIG. 2.
Figure 29:
FIG. 29 illustrates a screen displayed after an implementation result displayed on a display apparatus of FIG. 2 has been entered.

If the comparing of all of the implementation results against the condition has been completed (Y of S172), the selector 46 will display the selected implementation result on the display apparatus 64 (S174). FIG. 28 illustrates an initial screen, at a stage of recording/evaluation, displayed on the display apparatus 64. A patient selection button 200 to a recording/evaluation button 206 are displayed but the recording/evaluation button 206 is selected here. At this stage, no implementation result is displayed in the nursing record space 234. Though an implementation result window 280 is displayed in FIG. 28, this may not be displayed at all. The content displayed on the implementation window 280 corresponds to the sent content of the implementation result shown in FIG. 26. FIG. 29 illustrates a screen displayed after the implementation result displayed on the display apparatus 64 has been entered. Since the body temperature was selected here by the selector 46, the body temperature is displayed in the nursing record space 234 as the implementation result.

A description will now be given of an operation of the nursing information management system 10 structured as above. The nurse conducts a nursing action to a patient after confirming the nursing items displayed on the PDA 22. The nurse enters an implementation result into the PDA 22. The PDA 22 sends the implementation result to the PC 20. The PC 20 stores the received implementation result in the recording unit 60. If the variation of the implementation result stored is larger than a predetermined condition, the selector 46 will select this implementation result. The display apparatus 64 displays the selected implementation result.

By employing the above structure, at the time of displaying the implementation results, an implementation result is selected based on a predetermined condition and then displayed, so that as many necessary implementation results as possible can be displayed even though a display area provided for the implementation results is narrow. Since conditions to select the implementation results are stored beforehand, a condition required to select an implementation result that the nurse should look out for can be set. Since a condition is set for discrepancy between the implementation result in the past and the current implementation result, a case where the discrepancy in the implementation results is large can be selected. Also, even if a plurality of kinds of implementation results are defined, conditions corresponding respectively thereto are set, so that a necessary implementation result can be selected. Since an implementation result with less importance is not displayed on the screen, the verification of necessary information for the nurse becomes easier. Even in the case when the implementation result does not turn out to be desirable, the chance of overlooking it is low so as to give warning to the nurse. Also, the change of a nursing care plan can be reviewed.

6. Feedback and Entry of Variance

Feedback and entry of variance correspond to Step 22, Step 24 and Step 26 of FIG. 24. The problems to be resolved here may be indicated as follows. It is desired that the contents of evaluation be reflected in the nursing care plan. It is desired that the nursing care plan be suited to a patient. It is desired that a patient be recovered as soon as possible. It is desired that the actual information and the decision be displayed so that they can be clarified. Also, a factor causing the discrepancy between an implementation result of a nursing item and a target in the nursing item the implementation of which has been specified be analyzed.

In order to achieve a feedback and the input of variance, the viewing preparation unit 44, the display apparatus 64, the input control unit 50, the operation apparatus 62, the control unit 42, the management unit 56, the recording unit 60, the plan preparation supporting unit 34 and the counting unit 58 in FIG. 2 are principally used here.

6.1. Entry of Evaluations

The input control unit 50 receives an evaluation of an implementation result of a nursing items, from a nurse via the operation apparatus 62. Here, as described above, the evaluation is defined in the SOAP format. The recording unit 60 records the received evaluation. In so doing, the management unit 56 assigns to the evaluation an identification number of a nursing problem item corresponding to the evaluation. As a result, the nursing problem items stored in the recording unit 60, the nursing items included in the nursing care plan, the implementation results and the evaluations are brought into correspondence with one another by predetermined identification numbers. Such correspondence is shown in FIG. 3, for example.

The viewing preparation unit 44 has the received evaluations displayed on the display apparatus 64. The viewing preparation unit 44 divides the screen into at least two areas and displays S and O in a first area on the screen, which has been divided into at least two areas, and displays A and P in a second area by associating them with S and O displayed in the first area. That is, among the constituents included in the SOAP format, S and O corresponding to the information on the status of a patient and A and P corresponding to evaluations other than the information on the status of a patient are distinguished from each other and displayed on the screen accordingly. Hence, the distinction therebetween is clarified. The combination of S and O and the combination of A and P are brought into correspondence with each other, so that the relationship therebeween can be clarified.

6.2. Feedback

When receiving an evaluation from the nurse via the operation apparatus 62, the input control unit 50 receives the entry of a new nursing care plan in cooperation with the evaluation. More specifically, when entering P, the input control unit 50 receives a new nursing care plan that reflects the content of A. That is, the content of a nursing care plan which has not been entered is entered. While the entered nursing care plan is being managed by the management unit 56, it is recorded in the recording unit 60. When receiving the evaluation from the nurse, the input control unit 50 receives a specification about the completion or continuation of the nursing care plan. If a specification of the completion of the nursing care plan was received, the management unit 56 performs processing such as closing the information corresponding thereto in the nursing information recorded in the recording unit 60, and performs an end processing on the corresponding information.

If, on the other hand, a specification of the continuation of the nursing care plan was received, the information corresponding thereto in the nursing information recorded in the recording unit 60 continues to be effective. If the input control unit 50 receives a specification about the continuation of a nursing care plan, it will receive also a specification as to whether the nursing care plan is to be changed or not. If the nursing care plan is not to be changed, the nursing information recorded in the recording unit 60 will continue to be effective. If on the other hand, the nursing care plan is to be changed, the input control unit 50 will also receive contents of changes in the nursing care plan. The management unit 56 will reflect the changes in the nursing information recorded in the recording unit 60. Note that the plan preparation supporting unit 34 may reflect the received specification in the already prepared nursing care plan. In this manner, the contents of the evaluation are reflected in the nursing care plan.

6.3. Entry of Variance

If there is any discrepancy between the implementation results of nursing items and the targets in the nursing items specified to be implemented, the input control unit 50 receives also the input of variance factors when it receives evaluations from the nurse via the operation apparatus 62. A variance factor is said to represent information on a factor of discrepancy between the nursing care plan including a nursing target for a patient and the implementation result. The case where there is a discrepancy between an implementation result and a target in the nursing items specified to be implemented corresponds to a case where a recovery condition of a patient attended and a recovery condition of the patient which was planned beforehand differ and are apart from each other. That is, the discrepancy includes a case where the recovery is earlier than planned and a case where the recovery is slower than planned. In the case when there is any discrepancy, the management unit 56 presents a plurality of candidates for the variance factor to the nurse via the display apparatus 64. When the nurse selects any of the plurality of candidates via the operation apparatus 62, the management unit 56 receives the variance factor.

Figures 30, 31:
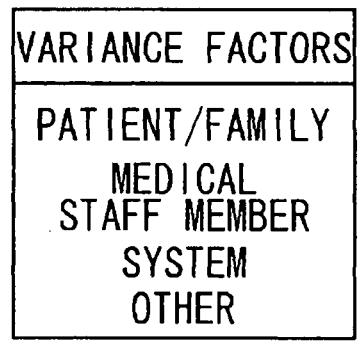
FIG. 30 is a data structure showing the candidates of a variance factor stored in a management unit of FIG. 2.
FIG. 31 illustrates a counting result recorded in a counting unit of FIG. 2.

FIG. 30 is a data structure showing the candidates for the variance factor stored in the management unit 56. Here, "patient/family", "medical staff member", "system" and "other" are defined as variance factors. The factor "patient/family" indicates that the variance is attributable to a patient and/or his/her family members. More specifically, a case where the curing is delayed because of diabetes, the patient's family members lack the understanding and so forth corresponds to this factor. In order to cope with this, the reviewing or reexamination of adaptation and therapeutic regimens will be effective. The factor "medical staff member" indicates that the variance is attributable to medical staff members. More specifically, a case where an incorrect drug is given, a patient is misidentified, an incorrect specification/instruction is given and so forth corresponds to this factor. In order to cope with this, educating the medical staff members and giving an on-the-job training (OJT) to them will be effective. The factor "system" indicates that the variance is attributable to systems. More specifically, a case where equipment malfunctions and the reservation is full corresponds to this factor. In order to cope with this, the efficient utilization of equipment and facilities will be effective. The factor "other" is attributable to factors other than the aforementioned. For example, social factors, the inability of securing a hospital to be transferred and the absence or inadequacy of domestic caring. In order to cope with this, the coordination of disease examination, the reviewing of a regulation for the number of hospital beds and home visiting nursing will be effective.

Furthermore, the management unit 56 presents to the nurse an open-ended entry space for the entry of an evaluation. This open-ended entry space corresponds to a space provided for giving a comment to the evaluation. The management unit 56 associates the comment in the open-ended entry space entered by the nurse with the selected variance factor. The thus associated comment in the open-ended entry space is stored in the recording unit 60. Also, as shown in FIG. 3, the recording unit 60 records the implementation results and the variance factors by associating them with the nursing care plans.

The counting unit 58 counts the number of variance factors stored in the recording unit 60, for each of a plurality of candidates regarding variance factors. That is, since "patient/family", "medical staff member", "system" and "other" are defined as a plurality of candidates, the counting unit 58 classifies the received variance factors into a plurality of candidates, respectively, and counts the number of variance factors for each of the plurality of candidates. In so doing, the counting unit 58 performs the counting by directing attention to the relationship between the implementation results and the targets. That is, when the number of variance factors received for one candidate, for example, "patient/family" is counted, the received variance factors are separated into positive variance factors and negative variance factors so as to conduct the counting. The positive variance factor is a variance factor for a case where the recovery is earlier than a target, and this corresponds to a variance factor which is to serve as a target for improvement. On the other hand, the negative variance factor is a variance factor for a case where the recovery is slower than the target, and this corresponds to a variance factor which needs to be improved.

FIG. 31 illustrates a counting result recorded in the counting unit 58. The counting result includes a variance space 170, a factor space 172 and a number-of-times space 174. In the variance space 170, variance factors are separated into positive factors and negative factors. Here, "+" corresponds to the positive factors and "−" the negative variance. The above-described plurality of candidates are respectively defined in the factor space 172. The number-of-times space 174 indicates the number of variance factors for each of the plurality of candidates. In the case of FIG. 31, there are many of "medical staff member" as the positive variance whereas there are many of "system" as the negative variance. From this counting result, it is concluded that "medical staff member" needs to be improved in order to make the recovery earlier than the target and "system" needs to be improved in order to improve the case where the recovery is slower than the target.

6.4. Operation

Figure 32:
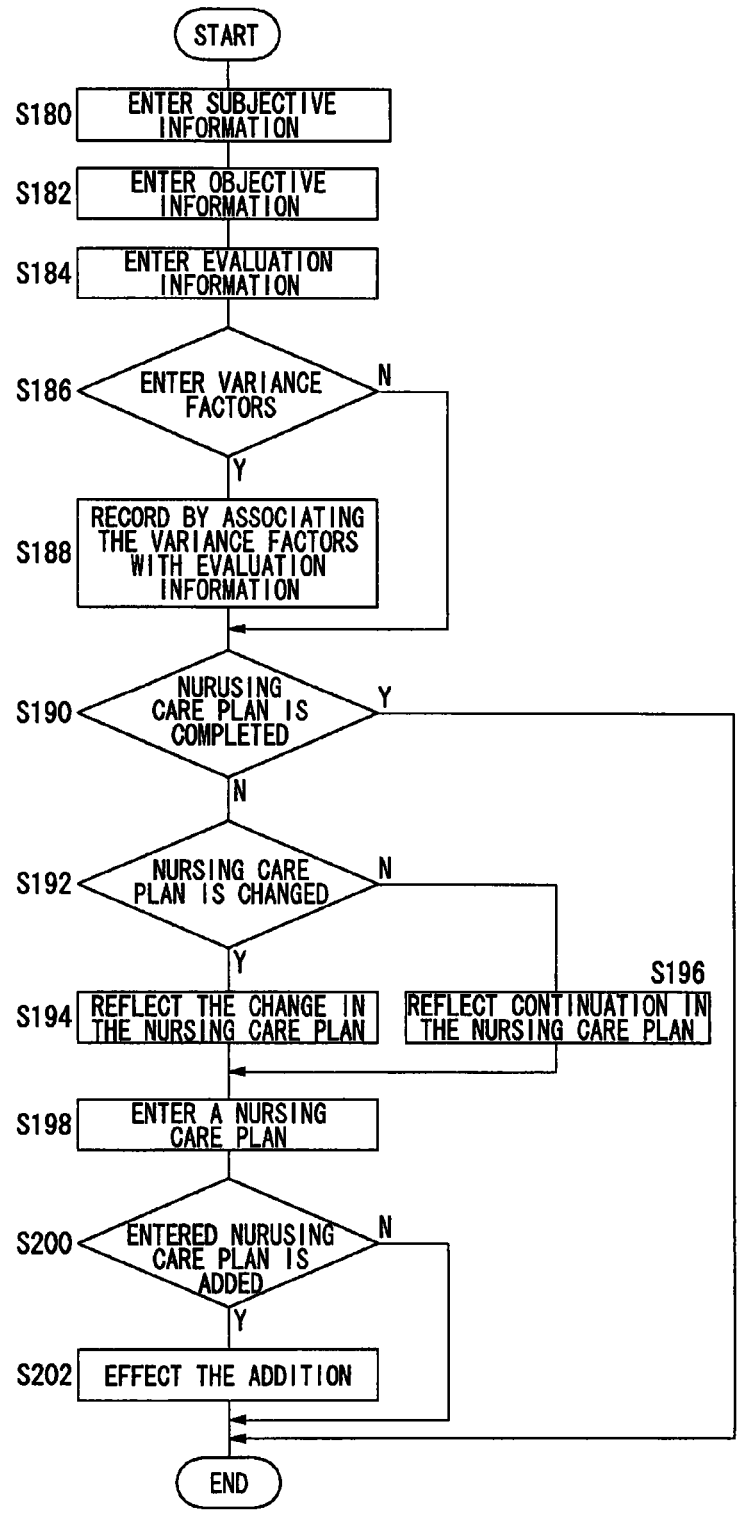
FIG. 32 is a flowchart showing a procedure for feedback processing in a PC of FIG. 2.
Figure 33:
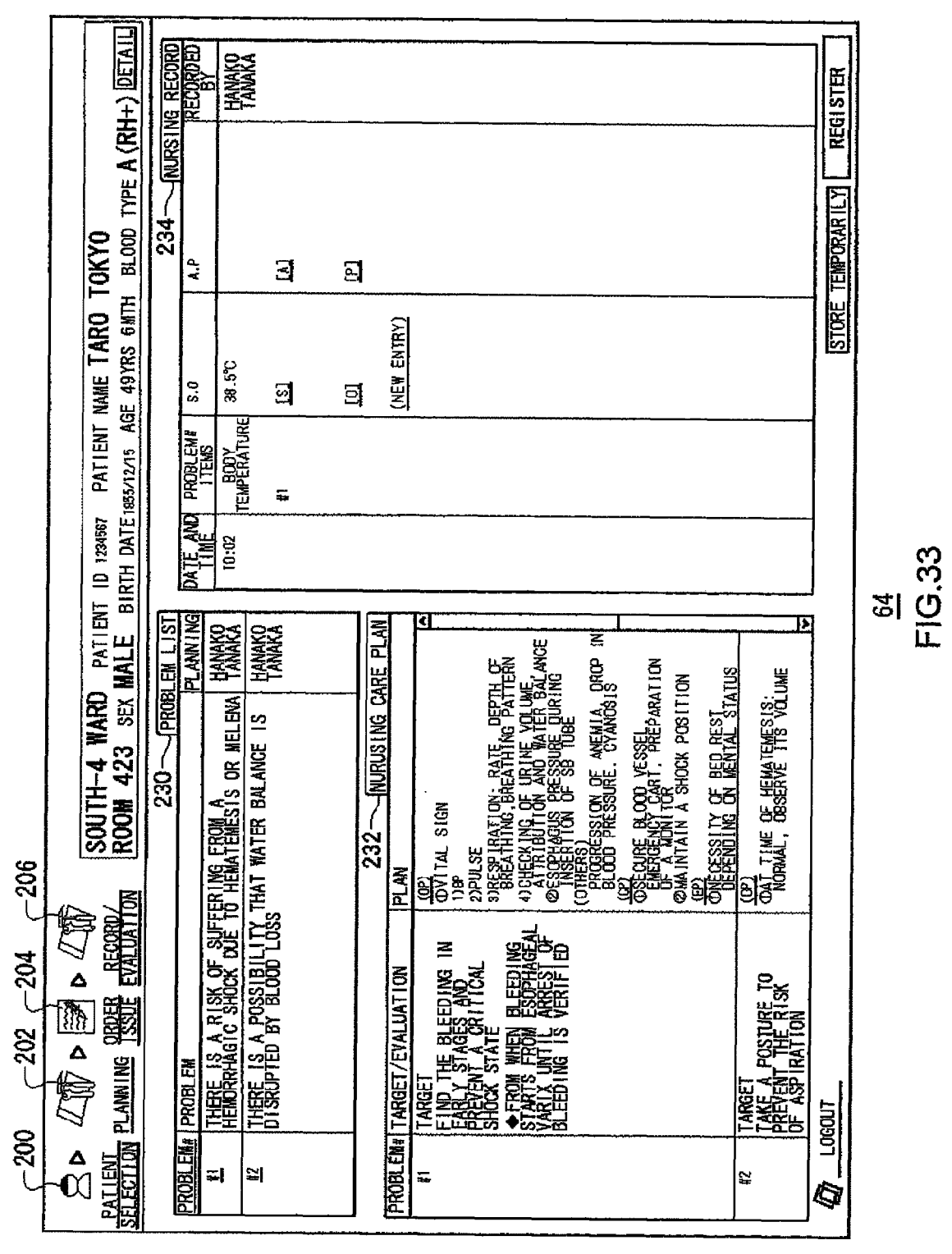
Figure 34:
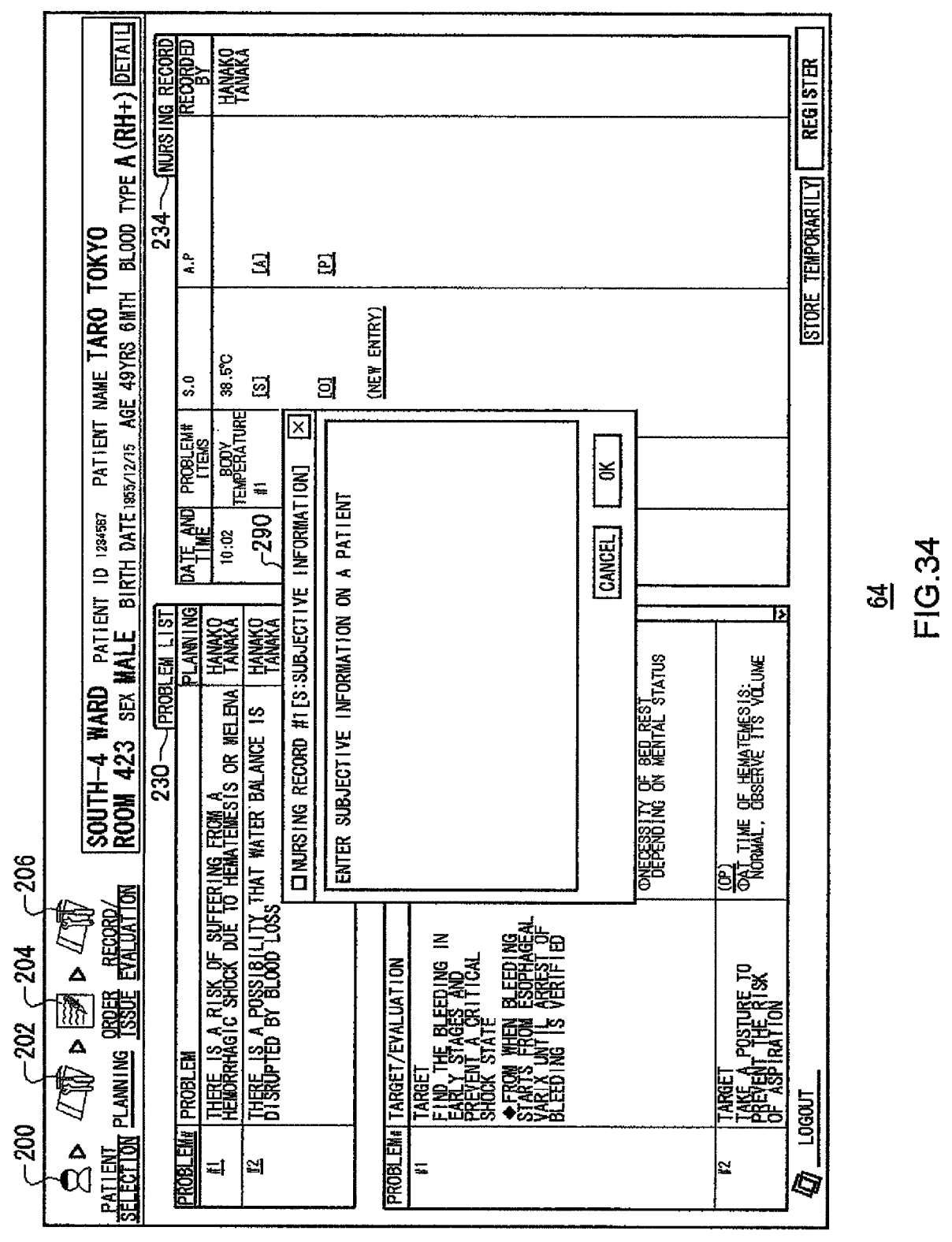

FIG. 32 is a flowchart showing a procedure for feedback processing in the PC 20. The input control unit 50 receives the entry of subjective information (S) via the operation apparatus 62 (S180). The received subjective information is recorded in the recording unit 60. FIG. 33 illustrates an initial screen obtained when an evaluation is entered and displayed on the display apparatus 64. FIG. 33 illustrates a screen at a stage before subjective information is entered. In FIG. 33, the recording/evaluation button 206 is selected, and areas to display "S", "O", "A" and "P" are provided in the nursing record space 234. FIG. 34 illustrates an entry screen of the subjective information displayed on the display apparatus 64. A subjective information entry window 290 is displayed in FIG. 34. The nurse enters subjective information using the operation apparatus 62.

Refer back to FIG. 32. The input control unit 50 receives the entry of objective information (O) via the operation apparatus 62 (S182). The received objective information is recorded in the recording unit 60. The same screen as that of FIG. 34 is displayed on the display apparatus 64. The input control unit 50 receives the entry of evaluation information (A) via the operation apparatus 62 (S184). The received evaluation information is recorded in the recording unit 60. FIG. 35 illustrates an entry screen of evaluation information displayed on the display apparatus 64. An evaluation information entry window 300 is displayed on the screen. The evaluation entry window 300 includes an open-ended entry space 302 and an evaluation/variance factor space 304. Using the operation apparatus 62, the nurse enters evaluation information into the open-ended entry space 302. Refer back to FIG. 32. If the input control unit 50 receives the entry of a variance factor (Y of S186), the recording unit 60 will record the received variance factor by associating it with the evaluation information (S188).

If, on the other hand, the input control unit 50 does not receive the entry of a variance factor (N of S186), proceed to the next step. In the evaluation/variance factor space 304 of FIG. 35, the entry of a variance factor is made by selecting any of a plurality of candidates including "patient/family" and so forth. Refer back to FIG. 32. If the input control unit 50 receives a specification to terminate a nursing care plan (P) (Y of S190), the processing will be terminated. If, on the other hand, the input control unit 50 does not receive a specification to terminate a nursing care plan (N of S190) and it receives a specification to change a nursing care plan (Y of S192), the management unit 56 or the plan preparation supporting unit 34 will reflect the change in the nursing care plan (S194). Also, the recording unit 60 records the changed nursing care plan. If the input control unit 50 does not receive a specification to change a nursing care plan (N of S192), the management unit 56 or the plan preparation supporting unit 34 will reflect the continuation thereof in the nursing record (S196).

Figure 36:
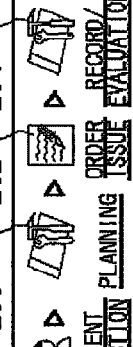
FIG. 36 illustrates a screen obtained after the evaluation information displayed on a display apparatus of FIG. 2 has been entered.

Such termination, continuation and change of a nursing care plan as described above are done by selecting any of "resolved", "continue" and "change" in the evaluation/variance factor space 304 of FIG. 35. FIG. 36 illustrates a screen obtained after the evaluation information displayed on the display apparatus 64 has been entered. FIG. 36 corresponds to a case where the continuation of a nursing care plan is specified. In FIG. 35, when the continuation thereof is selected, "continue" is displayed under "A" of the nursing record space 234. "Continue" is also displayed in "evaluation" of the nursing care plan space 232. Refer back to FIG. 32. The input control unit 50 receives the entry of a nursing care plan via the operation apparatus 62 (S198). Also, the received nursing care plan is recorded in the recording unit 60. Further, if the input control unit 50 receives a specification to add the inputted nursing care plan via the operation apparatus 62 (Y of S200), the management unit 56 or the plan preparation supporting unit 34 will implement the addition (S202).

Figure 37:
FIG. 37 illustrates an entry screen of a nursing care plan displayed on a display apparatus of FIG. 2.
Figure 38:
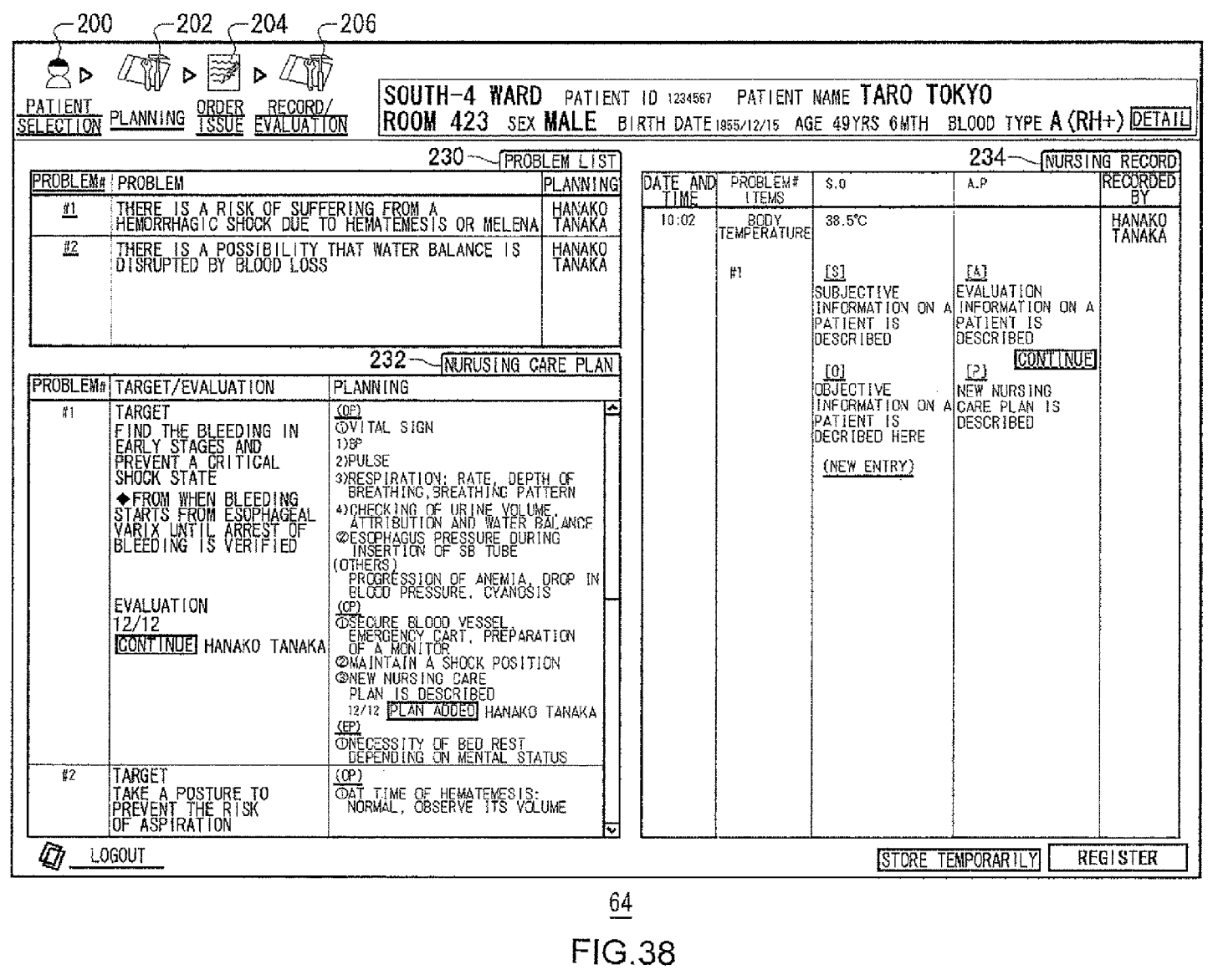

That is, the added nursing care plan is reflected in the nursing care plan space 232 displayed on the display apparatus 64. If, on the other hand, the input control unit 50 does not receive a specification to add the inputted nursing care plan via the operation apparatus 62 (N of S200), the processing will be terminated. FIG. 37 illustrates an entry screen of the nursing care plan displayed on the display apparatus 64. A nursing care plan window 310 is displayed on the screen. The nursing care plan window 310 includes an open-ended entry space 312 and a selection space 314. Using the operation apparatus 62, the nurse enters a nursing care plan into the open-ended entry space 312. Further, if the entered content is added to the nursing care plan space 232, a predetermined item contained in the selection space 314 is selected. FIG. 38 illustrates a screen obtained after the nursing care plan displayed on the display apparatus 64 has been entered. The content described in the open-ended entry space 312 of FIG. 37 is reflected in "P" in the nursing record space 234. Also, "plan added" is displayed in the nursing care plan space 232.

Figure 39:
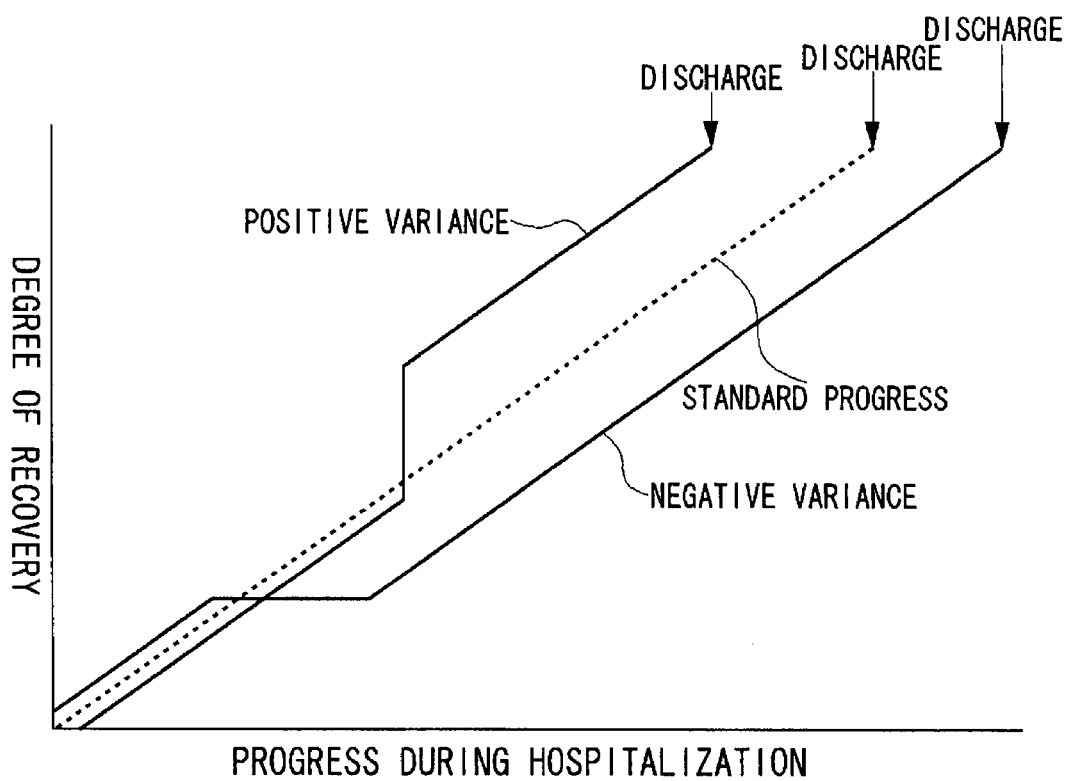
FIG. 39 is a graph to explain an effect of a variance analysis concerning an embodiment.

FIG. 39 is a graph to explain an effect of a variance analysis concerning the present embodiment. The horizontal axis in the graph indicates a progress during hospitalization, which means here the number of hospital stays. The vertical axis of the graph indicates the degree of recovery of a patient, and this means that the higher the position in the graph, higher the degree of recovery is. A "standard progress" indicated by a dotted line in the graph is a progression serving as a target when variance factors are entered. For clarity of the graph, the standard progress is indicated by a straight line here. The timing of discharge is indicated by an arrow mark. A positive variance corresponds to a case where the discharge timing is earlier than the standard progress. On the other hand, a negative variance corresponds to a case where the discharge timing is slower than the standard progress.

For a patient, a shorter duration of hospitalization is desired. The shorter the duration of hospitalization, smaller the expenditure in the hospital. As a result, the improvement of nursing contents by which to shorten the duration of hospitalization is desired. If the present progress indicates a negative variance, the variance factors at the present time will be analyzed and the nursing contents will be improved so that the progress is brought close to a positive variance. Such analysis of variance factors is performed by a medical institution or an external institution, based on the counting results in the counting unit 58. Finally, the duration of hospitalization can be reduced by bringing the present standard progress closer to a positive variance.

An operation of the PC 20 structured as above will be now be described. The nurse enters an evaluation of the nursing result in accordance with the SOAP format. Using the operation apparatus 62, the nurse also enters variance factors. Using the operation apparatus 62, the nurse further enters a new nursing care plan in connection with the evaluation. These pieces of information are recorded in the recording unit 60 by bringing them into correspondence with one another. Also, the counting unit 58 performs the counting for the variance factors.

By employing the structure described as above, a nursing care plan can be added in connection with the evaluation, so that the contents of the evaluation can be reflected in the nursing care plan. If a nursing care plan which is more suitable than the already prepared nursing care plan is added, the recovery of a patient will be facilitated. Since the added nursing care plan is also displayed in an area where the nursing care plan is to be displayed, the correspondence between the added contents and the contents already displayed can be clarified. Since the completion or continuation of a nursing care plan can be entered in connection with the evaluation thereof, the contents of the evaluation can be reflected in the nursing care plan while the contents of the evaluation is being verified. When the continuation thereof is selected, this is displayed accordingly, so that the contents of what has been selected is clarified. Since a change in the nursing care plan can be entered in connection with the evaluation, the nursing care plan can be modified to a more appropriate plan. Reflecting the contents of evaluation in the nursing care plan makes the nursing care plan more suitable. The recovery of a patient can be improved. The length of hospital stay for a patient can be shortened. When the evaluation is displayed, a combination of S and O and a combination of A and P are displayed separately, so that their differences can be clarified. Since the combination of S and O and the combination of A and P are displayed by associating one combination with the other, the correspondence therebetween can be clarified.

If there is any discrepancy between the implementation results of nursing items and the targets in the nursing items specifying the implementations, its contributing factors are entered, so that the contributing factors can be analyzed. By analyzing the contributing factors, the contents of a nursing care can be improved. Since the contents of a nursing care is improved, the duration of patient hospitalization can be shortened. Also, the hospital cost can be reduced. When the contributing factors are entered, candidates for the factors are also presented beforehand and a nurse is requested to select proper factors from among those candidates. Thus the entry of contributing factors can be simplified. Since the candidates for the factor are defined beforehand, the analysis of the contributing factors is facilitated. When the entered factors are gathered and counted, the counting is conducted by directing attention to a relationship with the implementation results, so that the level or characterization of the contributing factors becomes clear and a feedback of the contributing factors can be properly implemented. The entered factors are counted by dividing them into the categories of a positive variance and a negative variance, the improving measures for the nursing care best suited to a situation can be specified.

7. Preparation of Nursing Summaries

As described above, a nursing summary is prepared by a nurse. Since the contents of a nursing summary is generally determined by a nurse's discretion and assessment, the quality of the nursing summary differs every time the nurse prepares the nursing summary. Here, in order to keep the quality of such a nursing summary at a certain level, the following processing is performed. As the contents to be described in the nursing summary, the contents of "A" in "evaluation in the SOAP format" are particularly important. Accordingly, whenever a nursing summary is newly prepared, the contents of "A" is copied onto the entry screen of the nursing summary. As a result, the description of the nursing summary is facilitated, thus preventing the chance of failure to be described.

Generally the nursing summary is created at the time of "hospital discharge", "intermediate", "changing hospital" and "changing department". The "intermediate" is the timing at which the nursing summary shall be prepared on a regular basis in the case where a patient is scheduled to be hospitalized for a long period of time. For instance, this "intermediate" corresponds to the frequency of about once a month. Since there are cases where the nursing problems for a patient are all unresolved, the unresolved nursing problems (hereinafter also referred to as "remaining problems") should be described in the nursing summary, too. For this reason, the remaining problems are copied onto the entry screen of the nursing summary in addition to the contents of "A". By employing this scheme, the description of the nursing summary is facilitated, thus preventing the chance of failure to be described.

The operating apparatus 62 receives evaluations of implementation results of nursing items as the implementation contents of medical treatment for a patient. As described above, the evaluation is defined in the SOAP format. Also, the evaluations are associated with the nursing problems and the nursing care plans in the same manner as described above and hence the repeated explanation thereof is omitted here. The recording unit 60 records the evaluations received in the operating apparatus 62. The recording unit 60 also records the nursing problems as problems for patients to whom medical treatments are to be given.

When preparing the nursing summary, the management unit 56 verifies a status in the medical treatment for a patient. Here, the status corresponds to "hospital discharge", "intermediate", "changing hospital" and "changing department", for example. The management unit 56 may receive, via the operating apparatus 62, instructions indicating to select any of "hospital discharge", "intermediate", "changing hospital" and "changing department"

The management unit 56 extracts evaluation data related to an evaluation from among the implementation contents recorded in the recording unit 60. In particular, the management unit 56 extracts the contents "A" from those in the SOAP format. Although information on a plurality of patients is recorded in the recording unit 60, the management unit 56 extracts data on a desired patient according to an instruction from the operating apparatus 62. Also, the management unit 56 compares the nursing problems recorded in the recording unit 60 with the implementation results of the nursing problems, and extracts the remaining problems from among the nursing problem items. For instance, the nursing problems recorded are identified by the numbers "1" to "10" in the recording unit 60. If the evaluations corresponding to the numbers "7" to "10" are recorded, the management unit 56 will extract the nursing problems identified by the numbers "7" to "10" as the remaining problem data.

If a verified result belongs to "hospital discharge", the management unit 56 will prepare an initial edit content for a nursing summary by adding the extracted evaluation data to an edit area. Here, the edit area is structured by a storage medium such as memory. If the verified result belongs to other than "hospital discharge", the management unit 56 will prepare the initial edit content for a nursing summary by adding the remaining problem data in addition to the evaluation data. The management unit 56 displays the thus prepared initial edit contents on the display apparatus 64. Further, while verifying the initial edit contents displayed on the display apparatus 64, the nurse has the management unit 56 edit the initial edit contents via the operating apparatus 62. The management unit 56 displays the thus edited contents as the nursing summary. The management unit 56 manages items necessary for the preparation of the nursing summary. Data other than the above-described evaluation data and the remaining problem data may be managed as the necessary items. The management unit 56 compares the data added to the edit area (e.g., the above-described initial edit contents) with the necessary items, and prompts the addition of items which should have been added but are not yet added, so that a display indicating to instruct the addition is displayed on the display apparatus 64.

The recording unit 60 records the nursing summaries edited by the management unit 56. When displaying the nursing summaries or initial display contents, the viewing preparation unit 44 may display them in a manner that the remaining problem data added to the edit area in the management unit 56 are more emphasized than the other display contents.

Figure 40:
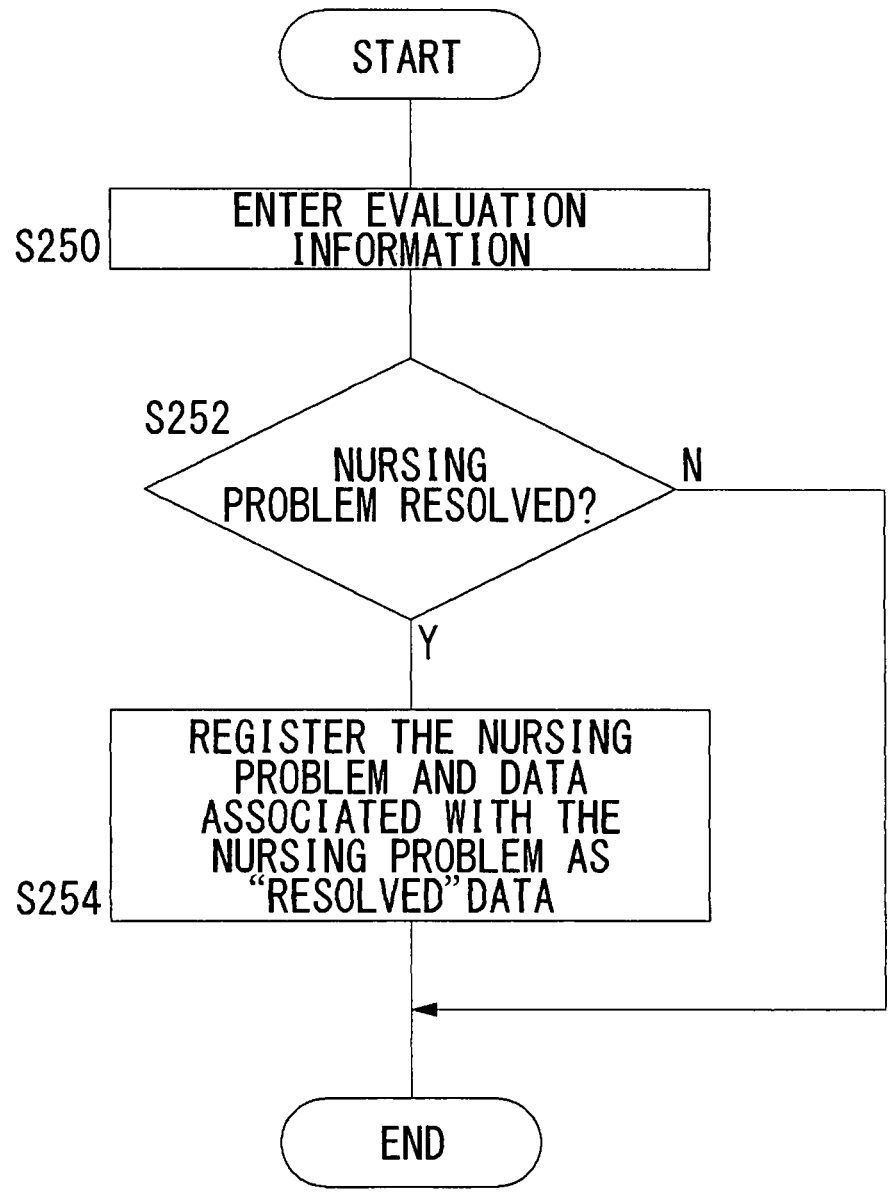
FIG. 40 is a flowchart showing a procedure for inputting evaluation information according to an embodiment.

FIG. 40 is a flowchart showing a procedure for inputting evaluation information according to the present embodiment. FIG. 40 corresponds to a preliminary step toward the preparation of a nursing summary, and corresponds to Step 184 of FIG. 32. The input control unit 50 receives the input of evaluation information (A) via the operating apparatus 62 (S250). The management unit 56 verifies whether the nursing problems have been resolved by the evaluation information or not (S252). For example, if a check mark is placed on a "resolved" space in the evaluation/variance factor space 304, the management unit 56 will determine that the nursing problems have been resolved. If the nursing problems have been resolved (Y of S252), the management unit 56 registers these nursing problems and the data corresponding thereto as "resolved" data among the information recoded in the recording unit 60 (S254) and then terminates the processing. If, on the other hand, the nursing problems have not been resolved (N of S252), the management unit 56 will terminate the processing.

Figure 41:
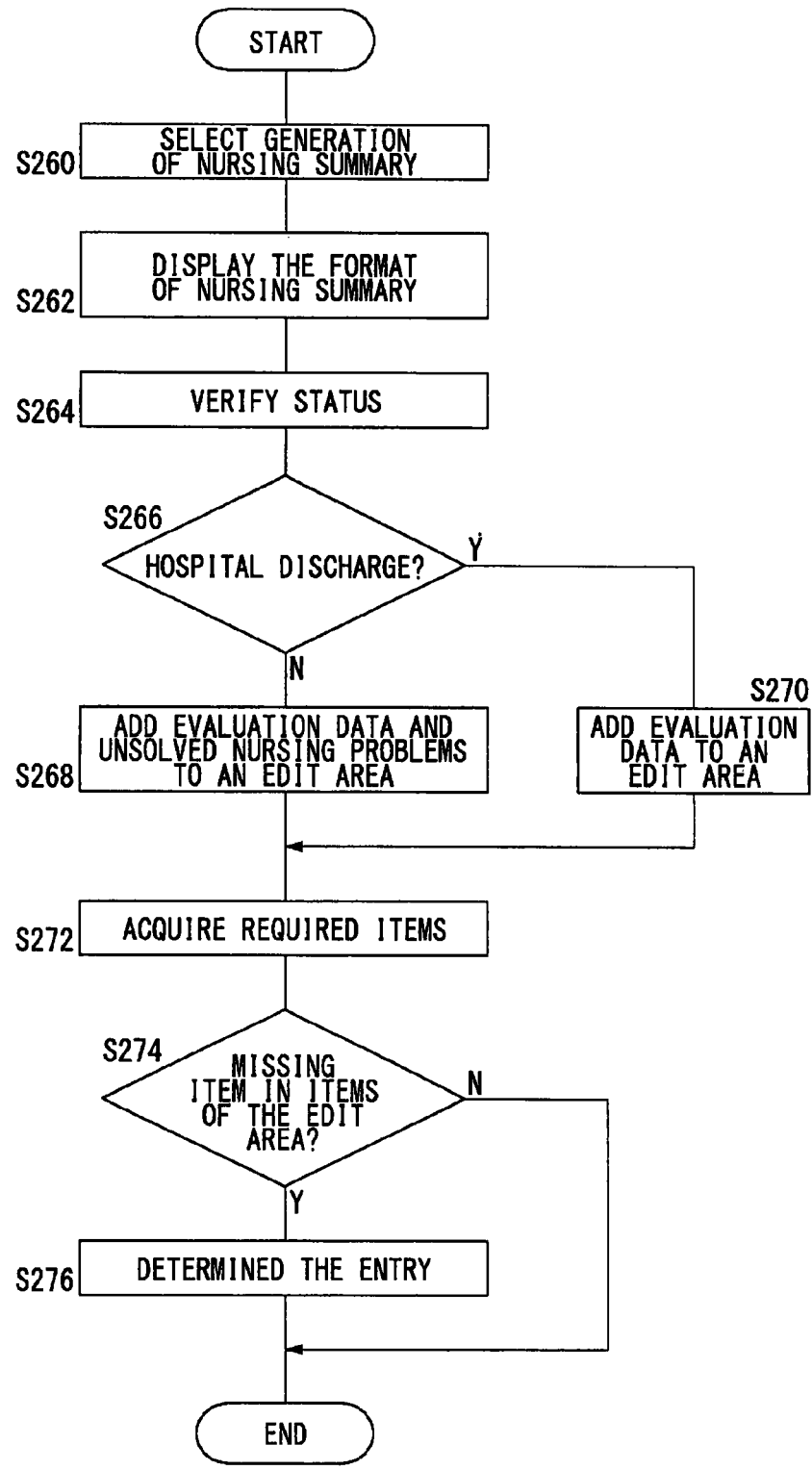
FIG. 41 is a flowchart showing a procedure for preparing a nursing summary according to an embodiment.
Figure 42:
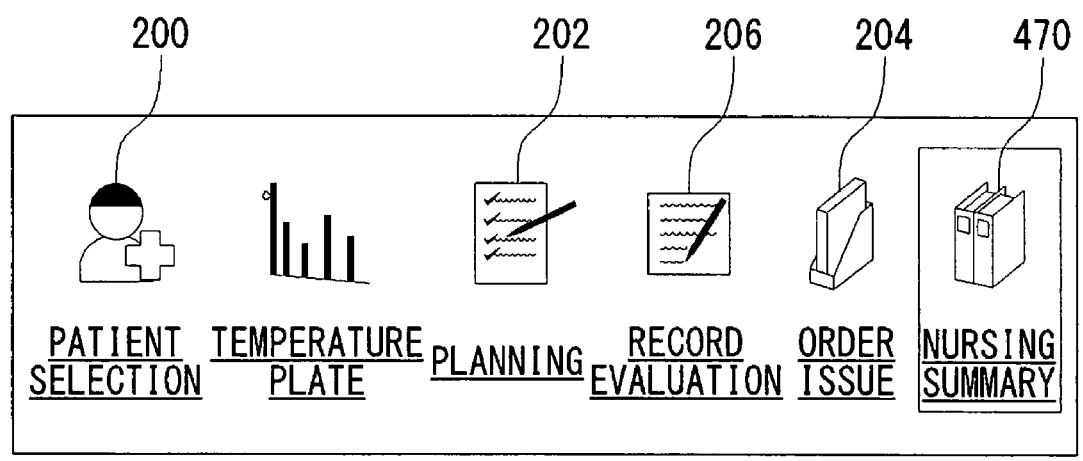
FIG. 42 illustrates a selection screen of a nursing summary displayed on a display apparatus of FIG. 2.

FIG. 41 is a flowchart showing a procedure for preparing a nursing summary according to the present embodiment. The input control unit 50 receives a selection indicating that a nursing summary is to be inputted (S260). FIG. 42 illustrates a selection screen of the nursing summary displayed on the display apparatus 64. FIG. 42 corresponds to an upper-left portion of the screen shown in FIG. 7 and shows a nursing summary button 470 in addition to the patient selection button 200 to the recording/evaluation button 206 of FIG. 7. The selection indicating that a nursing summary is to be inputted corresponds to the event that the nursing summary button 470 is selected by the nurse. Refer back to FIG. 41. Based on an instruction from the management unit 56, the viewing preparation unit 44 displays the format of the nursing summary on the display apparatus 64 (S262).

Figure 43:
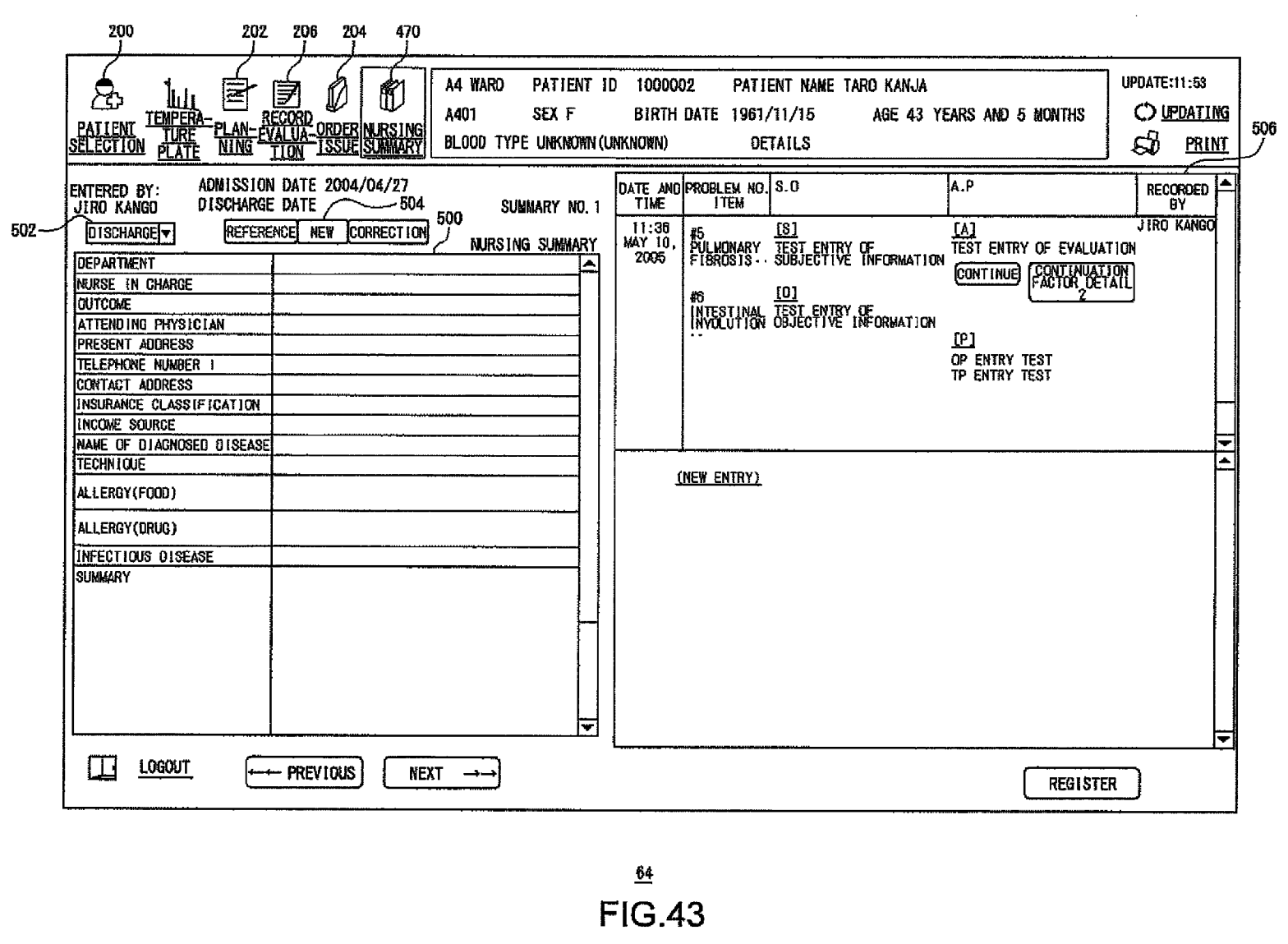

FIG. 43 illustrates an initial screen of the nursing summary displayed on the display apparatus 64. Displayed on the display apparatus 64 are not only a patient selection button 200 to a record/evaluation button 206, a nursing summary button 470 but also a nursing summary space 500, a status space 502, a new entry button 504 and a nursing record space 506. In the status space 502, the present status is selected. As the present status, one of "hospital discharge", "intermediate", "changing hospital" and "changing department" is selected. When the new entry button 504 is pressed by the nurse, the management unit 56 extracts desired data from the recording unit 60. Here, the nursing records displayed in the nursing record space 506 are used as a reference when the nursing summary is prepared, so that they cannot be modified or corrected even through the instruction given from the operating apparatus 62. A nursing summary is displayed in the nursing summary space 500. Refer back to FIG. 41.

The management unit 56 verifies the status (S264). When the new entry button 504 is pressed by the nurse in FIG. 4, the contents selected in the status space 502 are verified by the management unit 56. Refer back to FIG. 41. If the status belongs to the timing of hospital discharge (Y of S266), the management unit 56 will add the evaluation data, recorded in the recording unit 60, to an edit area (S270). If, on the other hand, the status is not a hospital discharge (N of S266), the management unit 56 will add the evaluation data recorded in the recording unit 60 and unresolved nursing problems to the edit area (S268). Here, the unresolved nursing problems correspond to the nursing problems which were not registered in Step S254 of FIG. 40.

Figure 44:
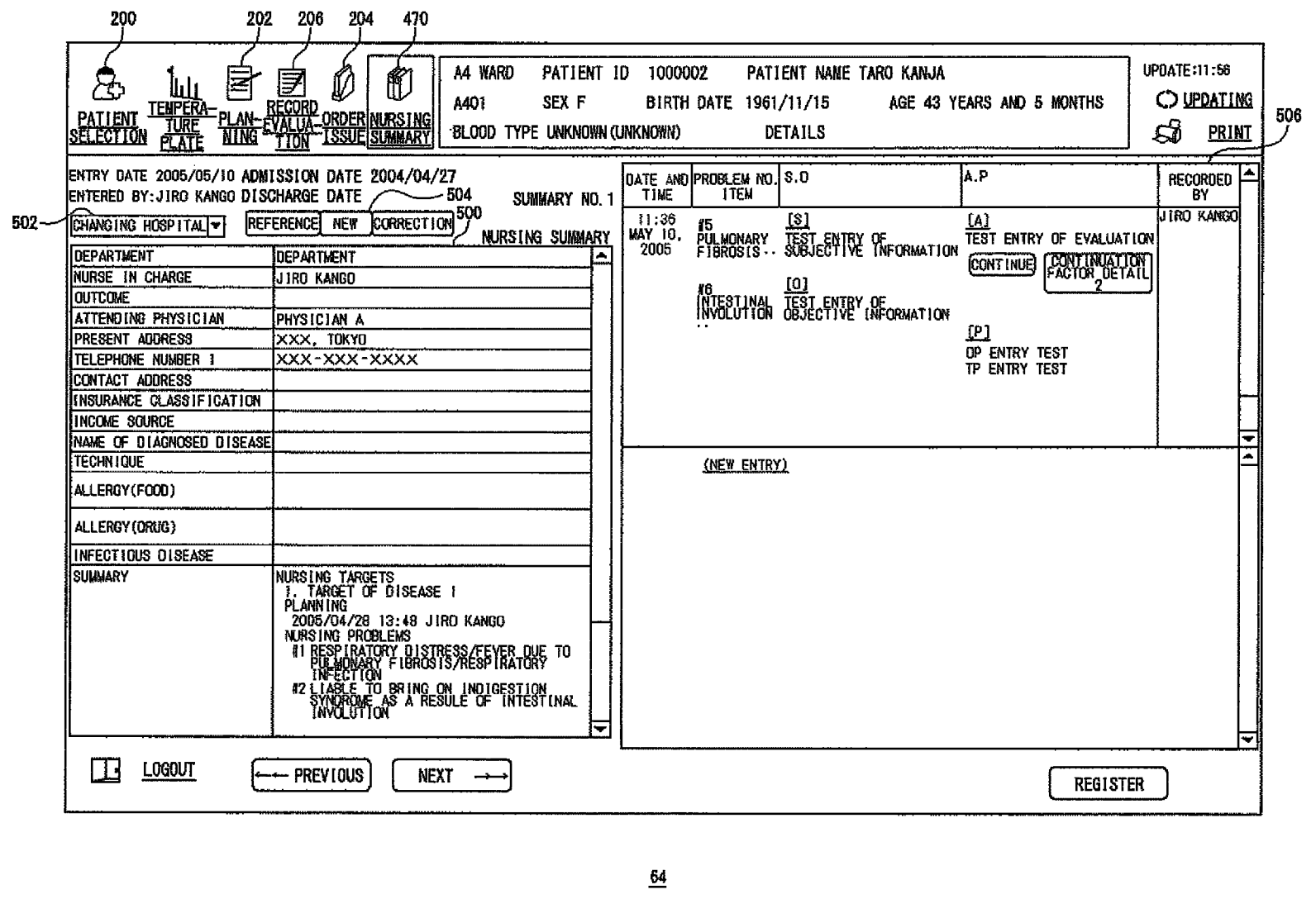

Then the management unit 56 acquires required items (S272). If any item is missing in the items which should appear in the edit area (Y of S274), the management unit 56 will prompt the entry thereof via the display apparatus 64 (S276), receive the entry thereof and then terminate the processing. If no item is missing in the edit area (N of S274), the management unit 56 will terminate the processing. Note that when terminating the processing, the management unit 56 may record a nursing summary in the edit area in the recording unit 60. FIG. 44 illustrates a screen of a nursing summary displayed on the display apparatus 64. Nursing summaries are displayed in the nursing summary space 500. Here, the remaining problem data and not-shown evaluation data are the nursing summaries. Also, nursing targets are registered as the required items, and the nursing targets are entered if prompted on the screen. Note that the nursing targets may be added to the initial edit contents.

When unresolved problems are extracted, there are cases where they have already been resolved but have not been registered yet. Accordingly, the management unit 56 may display the implementation contents for the unresolved nursing problems and the entry screen of the evaluation at the timing when the unresolved nursing problems are added to the edit area and then prompt the user to enter them. Also, though rare, there are cases where unresolved nursing problems still remain in the summary at the time of hospital discharge. For example, consider a case where an unresolved nursing problem has not yet been resolved but the treatment will continue by a home therapy. In such a case, the patient may be allowed to be discharged though the unresolved nursing problems are not yet resolved completely. Accordingly, based on the data concerning the unresolved nursing problems, the management unit 56 determines whether or not a discharge is possible even if there still exits any unresolved problems. If it is possible (for instance, if a home therapy is specified), the processing at Step 268 may be performed. If it is not possible, the implementation contents of nursing problems which have not been entered and the entry screen for entering the evaluation may be displayed.

By employing the structure described as above, the evaluation data are added to the edit area when the nursing summary is prepared. Thus, the evaluation data can be automatically added to the nursing summary and thereby the nursing summaries satisfying a certain quality level with required information described therein can be prepared. Also, the evaluation data are added to the edit area when the nursing summary is prepared, the burden placed on the nurse will be reduced. Also, since the remaining data are added in addition to the evaluation data, the problems for the patient which have to be resolved in the future can be clearly specified. Also, since the remaining data are added, the on-going nursing treatment can be reliably taken over. Also, since the type of data added to the edit area is changed according to the status, a nursing summary suited to the status can be prepared. Also, the remaining problem data are displayed in a manner that they are more emphasized than the other display contents, so that the attention can be drawn to the remaining problem data. The addition of an item which should be added but have not yet been added is prompted. Thus the items which should be added but have not yet been added can be prevented from not being added to the summary.

The present invention has been described based on the exemplary embodiments. These embodiments are merely exemplary, and it is understood by those skilled in the art that various modifications to the combination of each component and each process thereof are possible and that such modifications are also within the scope of the present invention.

In the embodiments of the present invention, the storage 48 stores predetermined conditions, and the selector 46 selects implementation results, satisfying the predetermined conditions, among the implementation results stored in the recording unit 60, and outputs their results to the viewing preparation unit 44. However, the present embodiments are not limited thereto and the selection of implementation results may be made manually. In such a case, the operation apparatus 62 receives from a nurse a specification about the listing of implementation results to be displayed in an area occupying a part of the screen, and performs a selection processing for selecting implementation results on the implementation results recorded in the recording unit 60, using the received specification as the predetermined conditions. This corresponds to a process where the implementation results to be selected are checked in the implementation result window 280 as shown in FIG. 28 and the result thereof is displayed in the nursing record space 234. According to this modification, a nurse's individual notion regarding the implementation results to be displayed can be reflected. That is, it suffices as long as a necessary and appropriate implementation result is selected.

In the embodiments of the present invention, the problem preparation supporting unit 30 outputs the nursing codes corresponding to the selected nursing problems, to the plan preparation supporting unit 34. Then the plan preparation supporting unit 34 selects nursing care plans from the second database 36, based on the nursing problem codes. However, the present embodiments are not limited thereto and, for instance, the problem preparation supporting unit 30 may output the selected nursing problem items to the plan preparation supporting unit 34 and the plan preparation supporting unit 34 may select nursing care plans from the second database 36, based on the nursing problem items. Alternatively, in the problem preparation supporting unit 30 and the plan preparation supporting unit 34, all of the processings may be carried out using codes corresponding to the nursing care plan items (hereinafter referred to as "nursing care plan codes"). In such case, for example, the coding problem codes or nursing care plan codes are converted into messages in the viewing preparation unit 44. According to this modification, the degree of freedom in the structure of the problem preparation supporting unit 30 and the plan preparation supporting unit 34 is improved. That is, it suffices if a nursing care plan corresponding to a nursing problem item is derived.

In the above-described embodiments of the present invention, a description has been given principally of a structure of the PC 20 but this structure may be provided for the server 12. In the present embodiments, the distinction between the PC 20 and the server 12 is made for convenience only, and it suffices if an apparatus connected to the PDA 22 has the above-described structure. According to this modification, the degree of freedom in the PC 20 and server 12 is improved.

While the preferred embodiments of the present invention have been described using specific terms, such description is for illustrative purposes only, and it is to be understood that changes and variations may be made without departing from the spirit or scope of the appended claims.

What is claimed is:
1. A medical treatment supporting system comprising;
    an input apparatus which receives implementation contents of a medical treatment performed on a patient;
    a first recording apparatus which records the implementation contents received by the input apparatus;
    an extraction unit of a computing apparatus which extracts evaluation data on an evaluation from the implementation contents recorded by the first recording apparatus;
    an editing unit of the computing apparatus which adds the evaluation data extracted by the extraction unit to an edit area and which edits a summary of an implementation result of the medical treatment;
    a second recording apparatus which records an editing result obtained by the editing unit;
    a nursing summary creation unit of the computing apparatus which requests creation of a nursing summary for the patient; and
    a verification unit of the computing apparatus which verifies whether the status of the patient is hospital discharge, intermediate, changing hospital, or changing department, when creation of a nursing summary is requested,
    wherein the first recording apparatus further records a problem for the patient to whom the medical treatment is to be performed,
    wherein the extraction unit extracts remaining unresolved problem data from among problems for the patient recorded in the first recording apparatus, by comparing the problem for the patient recorded in the first recording apparatus to whom the medical treatment is to be performed with the evaluation data extracted by the extraction unit, wherein when a verification result in the verification unit belongs to a case of a hospital discharge, the editing unit adds the evaluation data to the edit area without adding the remaining problem data, and, when the verification result in the verification unit indicates intermediate, changing hospital, or changing department, the editing unit further adds the remaining problem data to the edit area in addition to the evaluation data, wherein the implementation contents include data entered in SOAP (Subjective Objective Assessment Plan) format, and the evaluation data is an item in Assessment of the SOAP format, a display apparatus which displays the remaining problem data added to the edit data by the editing unit in a manner that the remaining problem data added thereto are more emphasized than other display contents, a management unit of the computing apparatus which manages items necessary for preparing the summary of an implementation result of the medical treatment, wherein the editing unit compares data already added to the edit area with the necessary items managed by the management unit, and prompts addition of an item which has not yet been added.

2. The medical treatment supporting apparatus according to claim 1, further comprising:

the management unit of the computing apparatus configured to determine whether hospital discharge of a patient is allowed even if there still exists any unsolved problem, based on data concerning unresolved nursing problems, wherein the management unit adds the recorded evaluation data and an unresolved nursing problem to the edit area, if hospital discharge is allowed, and displays an entry screen for entering contents and evaluation of a nursing problem not entered, if hospital discharge is not allowed.

3. A method for supporting a medical treatment, the method comprising:

receiving, with an input apparatus, implementation contents of a medical treatment performed on a patient;

recording, with a first recording apparatus, the received implementation contents;

extracting, with an extraction unit of a computing apparatus, evaluation data on an evaluation from the recorded implementation contents;

adding, with an editing unit of the computing apparatus, the extracted evaluation data to an edit area and editing a summary of an implementation result of the medical treatment; and requesting, with a requesting unit of the computing apparatus, creation of a nursing summary for the patient;

verifying, with the computing apparatus, whether the status of the patient is hospital discharge, intermediate, changing hospital, or changing department, when creation of a nursing summary is requested, wherein the first recording apparatus further records a problem for the patient to whom the medical treatment is to be performed, wherein the extracting unit extracts remaining unresolved problem data from among problems for the recorded patient, by comparing the problem for the recorded patient to whom the medical treatment is to be performed with the evaluation, wherein when a verification result belongs to a case of a hospital discharge, the editing unit adds the evaluation data to the edit area without adding the remaining problem data, and, when the verification result indicates intermediate, changing hospital, or changing department, the editing unit further adds the remaining problem data to the edit area in addition to the evaluation data, wherein the implementation contents include data entered in SOAP (Subjective Objective Assessment Plan) format, and the evaluation data is an item in Assessment of the SOAP format, displaying the remaining problem data added to the edit data in a manner that the remaining problem data added thereto are more emphasized than other display contents, managing items necessary for preparing the summary of an implementation result of the medical treatment, wherein the editing unit compares data already added to the edit area with the necessary items managed by the management, and prompts addition of an item which has not yet been added.

* * * * *